US012713192B2

(12) United States Patent
Rau et al.

(10) Patent No.: US 12,713,192 B2
(45) Date of Patent: Aug. 18, 2026

(54) METHOD AND APPARATUS FOR USING A GENERATIVE LARGE LANGUAGE MODEL FOR AUDIOLOGICAL FITTING AND DEVICE CONTROL

(71) Applicant: Sonova AG, Staefa (CH)

(72) Inventors: Richard Rau, Zurich (CH); Sebastian Krödel, Erlenbach (CH); Charlotte Vercammen, Horgen (CH); Nicola Hildebrand, Uster (CH); Michael Boretzki, Rüti (CH); Filip Wojcieszyn, Ottikon (CH); Stefan Klockgether, Hombrechtikon (CH); Julia Rehmann, Schmerikon (CH)

(73) Assignee: Sonova AG, Staefa (CH)

( * ) Notice: Subject to any disclaimer, the term of this patent is extended or adjusted under 35 U.S.C. 154(b) by 92 days.

(21) Appl. No.: 18/621,890

(22) Filed: Mar. 29, 2024

(65) Prior Publication Data

US 2025/0310708 A1 Oct. 2, 2025

(51) Int. Cl.

*G06F 40/40* (2020.01)
*G16H 40/67* (2018.01)
*H04R 25/00* (2006.01)

(52) U.S. Cl.

CPC ............. *H04R 25/70* (2013.01); *G06F 40/40* (2020.01); *G16H 40/67* (2018.01); *H04R 25/305* (2013.01); *H04R 25/505* (2013.01)

(58) Field of Classification Search

CPC .... H04R 25/70; H04R 25/305; H04R 25/505; H04R 2225/55; G06F 40/40
USPC ............. 381/312, 314; 704/2, 8–9, 246, 251
See application file for complete search history.

(56) References Cited

U.S. PATENT DOCUMENTS

| | | | | |
|---|---|---|---|---|
| 8,610,755 | B2 | 12/2013 | Brooksby et al. | |
| 2017/0132288 | A1* | 5/2017 | Ho | G06F 16/243 |
| 2018/0275956 | A1 | 9/2018 | Reed et al. | |
| 2019/0149927 | A1 | 5/2019 | Zhang et al. | |
| 2020/0066264 | A1 | 2/2020 | Kwatra et al. | |
| 2020/0219506 | A1 | 7/2020 | Bhowmik et al. | |
| 2021/0195343 | A1 | 6/2021 | Aubreville et al. | |
| 2022/0122606 | A1 | 4/2022 | Kamkar-Parsi et al. | |
| 2022/0360909 | A1 | 11/2022 | Reed et al. | |
| 2023/0037119 | A1 | 2/2023 | Ganot et al. | |

FOREIGN PATENT DOCUMENTS

| | | | |
|---|---|---|---|
| DE | 102018209719 | A1 | 7/2019 |
| WO | 2023028122 | A1 | 3/2023 |

* cited by examiner

*Primary Examiner* — George C Monikang
(74) *Attorney, Agent, or Firm* — Greenberg Traurig LLP

(57) ABSTRACT

A fitting apparatus for a hearing device includes a memory, the memory having stored thereon a plurality of embedding vectors and related solutions for possible hearing issues with a hearing or computing device. The fitting apparatus is configured to:

receive, via a user interface, a first signal indicative of a natural language input indicative of an issue experienced by a user;
determine an embedding based on the natural language input;
generate, based on the embedding, a first embedding vector;
determine a closest match between the first embedding vector and an embedding vector of the plurality of embedding vectors; and
send, to the user interface, a second signal indicative of a reply output, the reply output comprising information related to a solution of the related solutions for the issue experienced by the user.

20 Claims, 7 Drawing Sheets

14
30
32
10
12
20
22
24
18
15
16

14
10
12
36
68
60
62
66
64
24
20
22
40
42
44
46
48
50
52
80
82
84
86
88
90
70
72

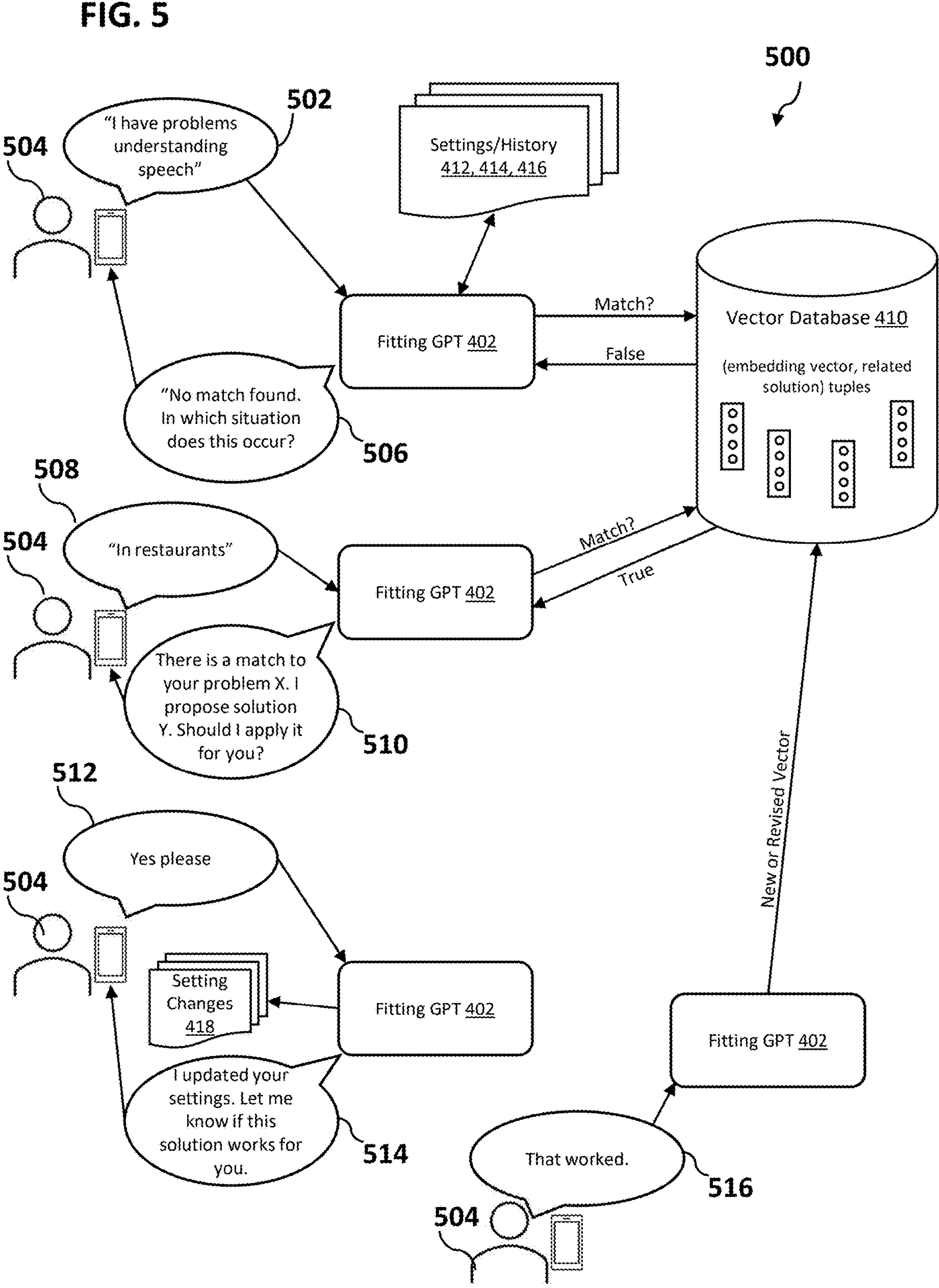
FIG. 5
500
502
504
"I have problems understanding speech"
Settings/History 412, 414, 416
Fitting GPT 402
Match?
False
Vector Database 410
(embedding vector, related solution) tuples
"No match found. In which situation does this occur?
506
508
504
"In restaurants"
Fitting GPT 402
Match?
True
There is a match to your problem X. I propose solution Y. Should I apply it for you?
510
512
Yes please
504
Setting Changes 418
Fitting GPT 402
I updated your settings. Let me know if this solution works for you.
514
New or Revised Vector
Fitting GPT 402
That worked.
516
504

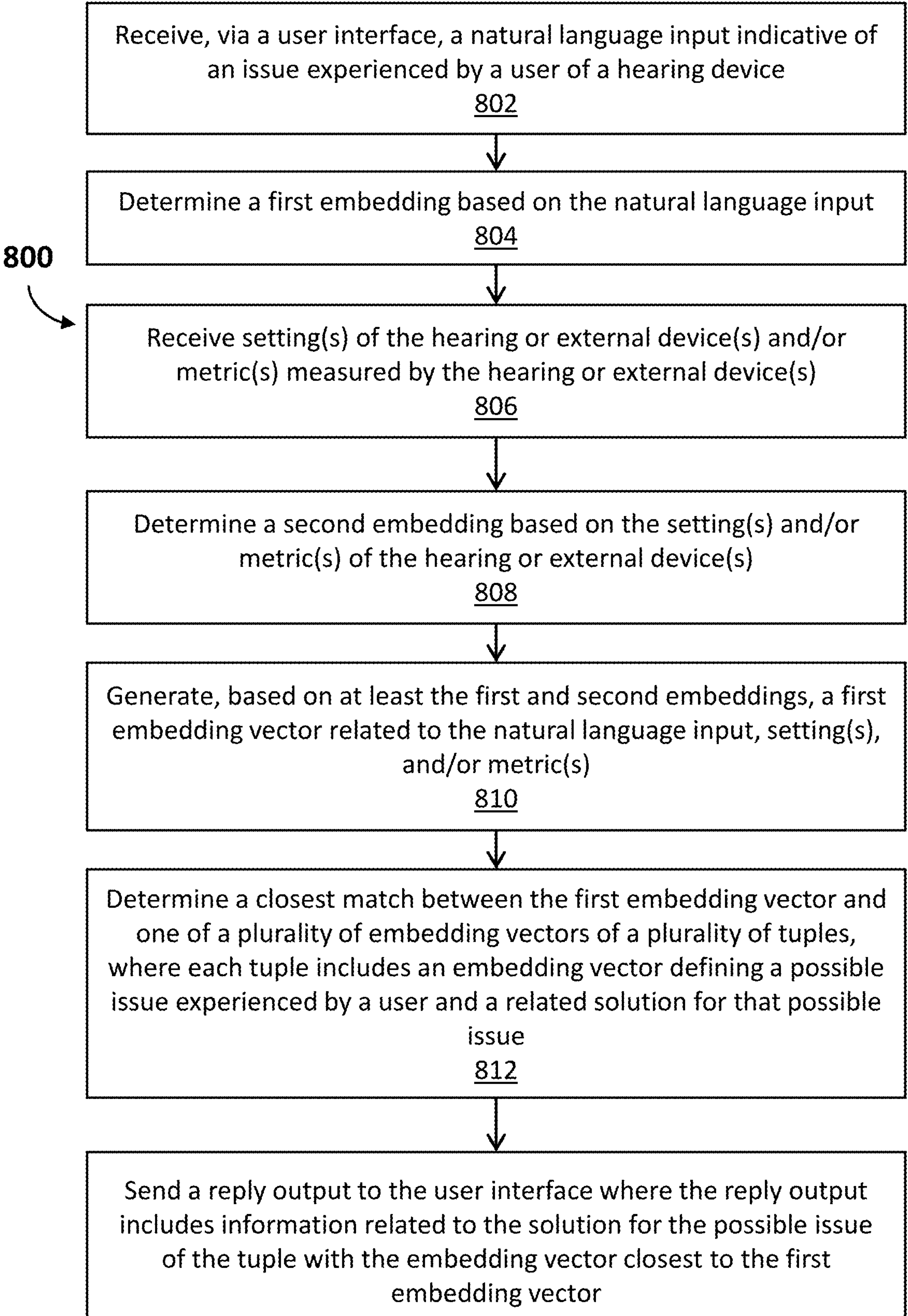
FIG. 8
800
Receive, via a user interface, a natural language input indicative of an issue experienced by a user of a hearing device
802
Determine a first embedding based on the natural language input
804
Receive setting(s) of the hearing or external device(s) and/or metric(s) measured by the hearing or external device(s)
806
Determine a second embedding based on the setting(s) and/or metric(s) of the hearing or external device(s)
808
Generate, based on at least the first and second embeddings, a first embedding vector related to the natural language input, setting(s), and/or metric(s)
810
Determine a closest match between the first embedding vector and one of a plurality of embedding vectors of a plurality of tuples, where each tuple includes an embedding vector defining a possible issue experienced by a user and a related solution for that possible issue
812
Send a reply output to the user interface where the reply output includes information related to the solution for the possible issue of the tuple with the embedding vector closest to the first embedding vector
814

Figure 9:
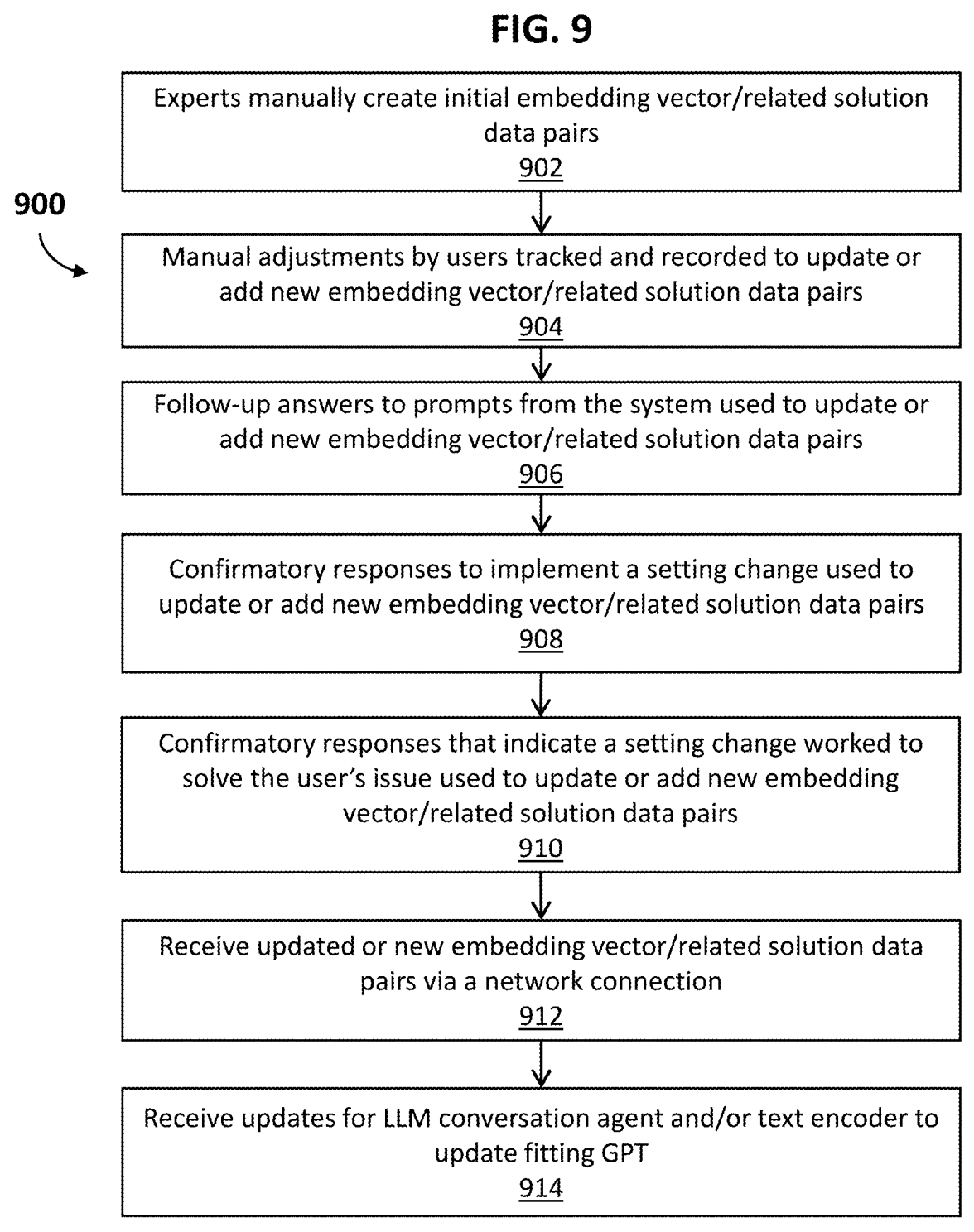

Experts manually create initial embedding vector/related solution data pairs
902

Manual adjustments by users tracked and recorded to update or add new embedding vector/related solution data pairs
904

Follow-up answers to prompts from the system used to update or add new embedding vector/related solution data pairs
906

Confirmatory responses to implement a setting change used to update or add new embedding vector/related solution data pairs
908

Confirmatory responses that indicate a setting change worked to solve the user's issue used to update or add new embedding vector/related solution data pairs
910

Receive updated or new embedding vector/related solution data pairs via a network connection
912

Receive updates for LLM conversation agent and/or text encoder to update fitting GPT
914

METHOD AND APPARATUS FOR USING A GENERATIVE LARGE LANGUAGE MODEL FOR AUDIOLOGICAL FITTING AND DEVICE CONTROL

TECHNICAL FIELD

The disclosure relates to methods and apparatuses for using a generative large language model for audiological fitting and device control, and more particularly to determining receiving natural language inputs from a hearing device user and suggesting and/or implementing changes to the operation or fitting of the hearing device or another related device to improve the experience of the user.

BACKGROUND

Hearing devices may be used to improve the hearing capability or communication capability of a user, for instance by compensating a hearing loss of a hearing-impaired user, in which case the hearing device is commonly referred to as a hearing instrument such as a hearing aid, or hearing prosthesis, or to adapt the sound to the preferences or the situational needs of a user. A hearing device may also be used to output sound based on an audio signal which may be communicated by a wire or wirelessly to the hearing device. A hearing device may also be used to reproduce a sound in a user's ear canal detected by an input transducer such as a microphone or a microphone array. The reproduced sound may be amplified to account for a hearing loss, such as in a hearing instrument, or may be output without accounting for a hearing loss, for instance to provide for a faithful reproduction of detected ambient sound and/or to add audio features of an augmented reality in the reproduced ambient sound, such as in a hearable. A hearing device may also provide for a situational enhancement of an acoustic scene, e.g. beamforming and/or active noise cancelling (ANC), with or without amplification of the reproduced sound. A hearing device may also be implemented as a hearing protection device, such as an earplug, configured to protect the user's hearing. Different types of hearing devices configured to be worn at an ear include earbuds, earphones, hearables, and hearing instruments such as receiver-in-the-canal (RIC) hearing aids, behind-the-ear (BTE) hearing aids, in-the-ear (ITE) hearing aids, invisible-in-the-canal (IIC) hearing aids, completely-in-the-canal (CIC) hearing aids, cochlear implant systems configured to provide electrical stimulation representative of audio content to a user, a bimodal hearing system configured to provide both amplification and electrical stimulation representative of audio content to a user, or any other suitable hearing prostheses. A hearing system comprising two hearing devices configured to be worn at different ears of the user is sometimes also referred to as a binaural hearing device. A hearing system may also comprise a hearing device, e.g., a single monaural hearing device or a binaural hearing device; a user device, e.g., a smartphone and/or a smartwatch, communicatively coupled to the hearing device; and/or an external device, e.g., a television connector, sound system connector, a Roger™ wireless microphone.

As such, hearing devices may be employed in conjunction with various user or external devices, which may take the form of smartphones or tablets, for instance when listening to sound data processed by the communication device and/or during a phone conversation operated by the communication device. More recently, communication devices have been integrated with hearing devices such that the hearing devices at least partially comprise the functionality of those user or external devices. A hearing system may therefore comprise, for instance, hearing device(s), user device(s), and/or external device(s).

SUMMARY

Since the first digital hearing aid was created in the 1980s, hearing aids have been increasingly equipped with the capability to execute a wide variety of increasingly sophisticated settings for hearing devices intended not only to account for an individual hearing loss of a hearing impaired user but also to provide for a hearing enhancement in rather challenging environmental conditions and according to individual user preferences. Those increased numbers and types of settings, however, may come at a cost that it is less easy to predict whether a desired goal of optimizing hearing for a user is met, e.g., when a user's environment changes and/or depending on the user's individual preferences.

As such, it is an object of the present disclosure to provide real time assistance to a user by (i) allowing a user to input natural language requests, issues, or other queries to a hearing system; (ii) process such natural language inputs from a user to derive useful information for presenting a solution to the user; (iii) implementing the solution by adjusting a setting of a hearing device or other user or external device; and (iv) improve the system by using feedback from the user and other data to update and further train the system. Previously, such adjustments may have been made by a healthcare professional upon a user consulting with and/or visiting the healthcare professional. With the various implementations described herein, a patient may determine and make their own adjustments to a hearing system in order to improve the experience of the user and prevent visits to a healthcare professional. The advantages of the implementations described herein can be achieved, for example, by an apparatus comprising the features of patent claim 1 and/or by a method comprising the features of patent claim 15. Further advantageous embodiments are defined by the dependent claims and the following description.

Accordingly, the present disclosure proposes a fitting apparatus for a hearing device comprising:

a processor; and a memory having stored thereon:

- non-transitory computer readable instructions executable by the processor, and
- a plurality of embedding vectors and related solutions for possible hearing issues with the hearing device or a computing device, and further wherein, upon execution of the instructions, the fitting apparatus is configured to:

- receive, via a user interface of the hearing device or the computing device, a first signal indicative of a natural language input, wherein the natural language input is indicative of an issue experienced by a user with the hearing device or the computing device;
- determine an embedding based on the natural language input;
- generate, based on the embedding, a first embedding vector;
- determine a closest match between the first embedding vector and an embedding vector of the plurality of embedding vectors; and
- send, to the user interface of the hearing device or the computing device, a second signal indicative of a reply output, the reply output comprising information related to a solution of the related solutions for the issue experienced by the user.

Thus, by generating a first embedding vector from a natural language input from a user and comparing that first embedding vector to the plurality of embedding vectors defining possible issues and associated with related solutions for possible hearing issues, a closest embedding vector of one of the plurality of embedding vectors to the first embedding vector related to the natural language input can be determined. The related solution associated with the closest embedding vector of the plurality of embedding vectors can then be presented to the user, implemented by changing a setting of a device, etc. The fitting apparatus as described herein may be any computing device (or combination of computing devices) on which instructions for running a corresponding fitting software are stored and/or executed (e.g., a personal computer; table computing device; computer terminal; distributed computer system including some or all of servers, clients, etc. communicating over the internet, an intranet, or any other network; mobile computing devices such as mobile phones, dedicated handheld devices, wearable devices (e.g. smartwatches, smart glasses, etc.); a hearing device, user device, and/or external device as described herein itself/themselves; etc.). Similarly, the methods for fitting a hearing device described herein may also be implemented using any such computing device (or combination of computing devices).

Independently, the present disclosure also proposes a method for fitting a hearing device comprising:

- receiving, by a processor via a user interface of the hearing device or a computing device, a first signal indicative of a natural language input, wherein the natural language input is indicative of an issue experienced by a user with the hearing device or the computing device;
- determining, by the processor, a first embedding based on the natural language input;
- receiving, by the processor, a second signal indicative of:
  - a setting of the hearing device or the computing device, or
  - a metric measured by the hearing device or the computing device;
- determining, by the processor, a second embedding based on the setting or the metric;
- generating, by the processor based on the first embedding and the second embedding, a first embedding vector;
- determining, by the processor, a closest match between the first embedding vector and an embedding vector of an embedding vector of a plurality of embedding vectors, wherein each of the plurality of embedding vectors is associated with one of a plurality of related solutions for possible hearing issues with the hearing device or the computing device; and
- sending, by the processor to the user interface of the hearing device or the computing device, a third signal indicative of a reply output, the reply output comprising information related to a solution of the related solutions for the issue experienced by the user.

Thus, the embedding vector generated from a natural language input from a user can further incorporate (i) settings of a hearing device or other device being used by a user (e.g., what type of devices the user is using, what the current audio processing settings of those devices are) and/or (ii) metrics measured by a hearing device or other device being used by a user (e.g., noise present in an environment, etc.). As such, additional dimensions can be added to the determined embedding vector for each of the different types of settings and/or metrics considered, adding more complexity and accuracy to the matching of the determined embedding vector to the plurality embedding vectors and related solutions stored in a database (e.g., the system is able to consider more factors and determine better solutions for the user).

The present disclosure also proposes a non-transitory computer-readable medium storing instructions for fitting a hearing device that, when executed by a processor, which may be included in a hearing device, user device, external device, and/or a hearing system, cause a hearing device and/or a hearing system to perform operations of any of the methods or apparatuses described herein.

Subsequently, additional features of some implementations of the method of operating a hearing device and/or the hearing device are described. Each of those features can be provided solely or in combination with at least another feature. The features can be correspondingly provided in some implementations of the methods and/or apparatuses described herein.

In some implementations, wherein the embedding is a first embedding, and wherein the fitting apparatus for the hearing device is further configured to, upon execution of the instructions:

- receive a third signal indicative of a setting of the hearing device or the computing device; and
- determine a second embedding based on the setting, wherein the first embedding vector is generated based on both the first embedding and the second embedding.

In some implementations, the fitting apparatus for the hearing device wherein the setting of the hearing device or the computing device comprises at least one of:

- a fitting parameter set of a hearing device;
- a type of the hearing device;
- a coupling setting or type of the hearing device;
- a feedback threshold of the hearing device;
- a real ear transfer function setting of the hearing device;
- a target gain of the hearing device;
- actual gain of the hearing device;
- an actuator setting of the hearing device;
- actual feedback stability of the hearing device; or
- a hardware test parameter of the hearing device.

In some implementations, wherein the fitting apparatus for the hearing device is further configured to, upon execution of the instructions:

- receive a fourth signal indicative of a metric measured by the hearing device or the computing device; and
- determine a third embedding based on the setting, wherein the first embedding vector is generated based on both the first embedding, the second embedding, and the third embedding.

In some implementations, the fitting apparatus for the hearing device wherein the metric comprises at least one of:

- a signal level;
- a noise floor estimation;
- a signal-to-noise ratio;
- a classification of a sound source; or
- an estimated listening intention.

In some implementations, the fitting apparatus for the hearing device wherein the computing device comprises at least one of a user device or an external device.

In some implementations, the fitting apparatus for the hearing device wherein the natural language input further comprises temporal information related to the issue experienced by the user, the temporal information indicative of whether the issue is being currently experienced or was previously experienced by the user.

In some implementations, wherein the fitting apparatus for the hearing device is further configured to, upon execution of the instructions:

receive, via the user interface of the hearing device or the computing device, a third signal indicative of a confirmatory response to the reply output, the confirmatory response indicative of a user assent to implementing the solution; and implement the solution in the hearing device or the computing device, or send an instruction to implement the solution to the hearing device or the computing device.

In some implementations, wherein the fitting apparatus for the hearing device is further configured to, upon execution of the instructions:

send, to the user interface of the hearing device or the computing device, a third signal indicative of a request to confirm an efficacy of the solution for the issue; and receive, via the user interface of the hearing device or the computing device, a fourth signal indicative of a confirmatory response to the request.

In some implementations, wherein the fitting apparatus for the hearing device is further configured to, upon execution of the instructions, update the plurality of embedding vectors and/or the related solutions based on the confirmatory response to the request.

In some implementations, wherein the fitting apparatus for the hearing device is further configured to, upon execution of the instructions:

send, prior to sending the second signal indicative of the reply output, a third signal indicative of a follow-up request to the user interface of the hearing device or the computing device, wherein the follow-up request requests more information related to the issue experienced by the user; and receive, via the user interface of the hearing device or the computing device, a fourth signal indicative of a follow-up answer to the follow-up request, wherein the first embedding vector is further determined at least in part based on the follow-up request.

In some implementations, the fitting apparatus for the hearing device wherein the embedding based on the natural language input comprises embeddings related to multiple dimensions, wherein the first embedding vector is indicative of values associated with each of the embeddings related to multiple dimensions.

In some implementations, the fitting apparatus for the hearing device wherein the natural language input comprises at least one of:

text entered by the user through a keyboard of the user interface of the hearing device or the computing device; or speech spoken by the user and sensed by a sound detector of the hearing device or the computing device.

In some implementations, the fitting apparatus for the hearing device wherein each of the plurality of embedding vectors and the related solutions are manually defined based on previously identified problems with hearing devices and the previously identified problems' respective solutions.

In some implementations, wherein the fitting apparatus for the hearing device is further configured to, upon execution of the instructions:

determine, based on first signal indicative of the natural language input, a translation of the natural language input; and send, to a computing device associated with a health care provider, a third signal indicative of the translation.

BRIEF DESCRIPTION OF THE DRAWINGS

Reference will now be made in detail to embodiments, examples of which are illustrated in the accompanying drawings. The drawings illustrate various embodiments and are a part of the specification. The illustrated embodiments are merely examples and do not limit the scope of the disclosure. Throughout the drawings, identical or similar reference numbers designate identical or similar elements. In the drawings:

FIG. 5 schematically illustrates an example flow of messaging between a user device and a hearing system;

FIG. 8 schematically illustrates a flow chart for processing natural language inputs from a user to determine a solution to a possible issue related to the natural language inputs;

FIG. 9 schematically illustrates a flow chart for initially establishing a vector database and further training the vector database after establishment.

DETAILED DESCRIPTION OF THE DRAWINGS

Figures 1, 2:
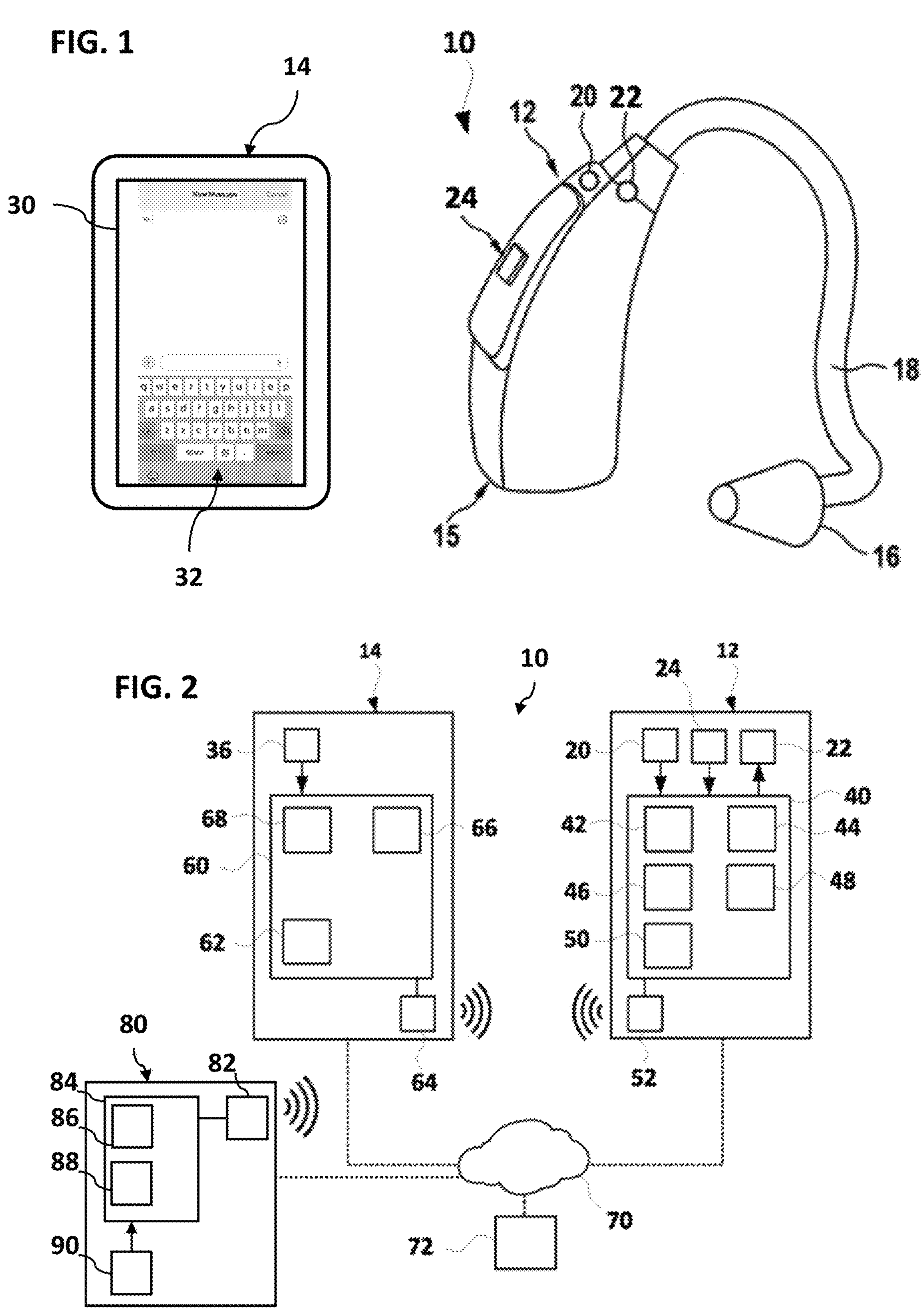
FIG. 1 schematically illustrates a hearing system.
FIG. 2 schematically illustrates a block diagram of components of the hearing system according to FIG. 1.

FIG. 1 schematically shows a hearing system 10 according to an embodiment of the invention. The hearing system 10 includes a hearing device 12 and a user device 14 connected to the hearing device 12. As an example, the hearing device 12 is formed as a behind-the-ear device carried by a user (not shown) of the hearing device 12. It has to be noted that the hearing device 12 is a specific embodiment and that the method described herein also may be performed with other types of hearing devices, such as e.g. earbuds, earphones, hearables, and hearing instruments such as receiver-in-the-canal (RIC) hearing aids, in-the-ear (ITE) hearing aids, invisible-in-the-canal (IIC) hearing aids, completely-in-the-canal (CIC) hearing aids, cochlear implant systems configured to provide electrical stimulation representative of audio content to a user, a bimodal hearing system configured to provide both amplification and electrical stimulation representative of audio content to a user, or any other suitable hearing prostheses; and a hearing system for a user may include one or two of the hearing devices 12 mentioned above. The user device 14 may be a smartphone, a tablet computer, smart glasses, etc.

The hearing device 12 comprises a first part 15 behind or at the ear (which may also be referred to as a behind-the-ear (BTE) part) and a second part 16 to be put in the ear canal of the user (which may also be referred to as an in-the-ear (ITE) part). The first part 15 and the second part 16 are connected by a tube 18 or cable. A cable may be used in a receiver-in-the-canal (RIC) hearing device, for example. The first part 15 comprises at least one sound detector 20, e.g. a microphone or a microphone array, a sound output component 22 (which may also be referred to as a receiver), such as a loudspeaker, and optionally an input 24, e.g. a knob, a button, or a touch-sensitive sensor, e.g. capacitive sensor. The sound output component 22 may also be integrated into the second part 16. The sound detector 20 can detect a sound in the environment of the user and generate an audio signal indicative of the detected sound. Such an audio signal may be, for example, a voice of the user or another person such that speech of a user may be detected and identified as a natural language input as described herein. The sound detector 20 may also be a sensor that is used to measure one or more metrics of a hearing situation (e.g., a signal level, a noise floor estimation, a signal-to-noise ratio, classified sound sources, an estimated listening intention etc.), and such metrics may be used as dimensions to determine an embedding vector as described herein. The sound output component 22 can output sound based on the audio signal modified by the hearing device 12 in accordance with the hearing device settings, wherein the sound from the sound output component 22 is guided through the tube 18 to the second part 16 in a BTE hearing device. In other embodiments, such as an RIC hearing device, a sound output component may be ITE and an audio signal modified by the RIC hearing device may be transmitted through a cable to a sound output component ITE. The input 24 enables an input of the user into the hearing device 12, e.g. in order to power the hearing device 12 on or off, and/or for choosing a sound program, hearing device settings, or any other modification of the audio signal. In various embodiments, the input 24 may or may not be present on the hearing device 12 itself, and a user input may be made additionally or alternatively through another device, such through a mobile application (app) on the user device 14 (e.g., a tablet computer, mobile or smart phone, smart glasses, smartwatch, etc.). In various embodiments, an action such as powering the hearing device 12 on or off, choosing a sound program of the hearing device 12, choosing a setting of the hearing device 12, etc. may also be performed automatically by the hearing device 12 or another device such as the user device 14. Hearing device settings may be changed based on the methods and apparatuses described herein, such as based on outputs of a fitting generative pre-trained transformer (GPT) as described herein that are responsive to a natural language input of a user (e.g., where the user's natural language input is fitted to a solution by the fitting GPT).

The user device 14, which may be a smartphone, a tablet computer, smart glasses, smartwatch, etc. may include a display 30, e.g. a touch-sensitive display, providing a graphical user interface 32 including control element 32, e.g. a keyboard for entering natural language text, which may be controlled via a touch on the display 30. The user device 14 may further include a sound detector or microphone (not shown) for receiving speech from a user that may be used as the natural language input described herein. The control element 32 may be referred to as an input, a user interface, or a graphical user interface of the user device 14. Various user devices 14 may comprise a knob or button instead of or in addition to a touch-sensitive display as shown in FIG. 1.

FIG. 2 shows a block diagram of components of the hearing system 10 according to FIG. 1. The hearing device 12 comprises a first processing unit 40 (e.g., a processor). The first processing unit 40 may, in various embodiments, implement in part or in whole the various methods described herein to receive and process natural language inputs from a user. The first processing unit 40 is also configured to receive the audio signal generated by the sound detector 20.

The hearing device 12 may include a sound processing module 42. For instance, the sound processing module 42 may be implemented as a computer program executed by the first processing unit 40, which may comprise a central processing unit (CPU) (e.g., a processor) for processing the computer program as well as other instructions stored on a memory or electronic storage. Alternatively, the sound processing module 42 may comprise a sound processor implemented in hardware or a more specific a DSP (digital signal processor) for modifying the audio signal. The sound processing module 42 may be configured to activate/deactivate, modify, amplify, dampen, and/or delay the audio signal generated by the sound detector 20, e.g. some frequencies or frequency ranges of the audio signal depending on parameter values of parameters, which influence the amplification, the damping and/or, respectively, the delay, e.g. in correspondence with a current sound program. The parameter may be one or more of the group of frequency dependent gain, time constant for attack and release times of compressive gain, time constant for noise canceller, time constant for dereverberation algorithms, reverberation compensation, frequency dependent reverberation compensation, mixing ratio of channels, gain compression, gain shape/amplification scheme. A set of one or more of these parameters and parameter values may correspond to a predetermined sound program included in hearing device settings. In various embodiments, these parameters or other functions of the sound processing module 42 may be modified in response to determinations made by the various embodiments described herein in response to natural language inputs from a user (e.g., any aspect or parameter associated with the audio processing may be adjusted based on a matching tuple or embedding vector determined by the system to be a closest match to an embedding vector generated based on a natural language input from a user or user device).

In general, sound program hearing device settings may be defined by parameters and/or parameter values defining the sound processing of the sound processing module 42, such as the parameters described above. Different sound programs hearing device settings are then characterized by correspondingly different parameters and parameter values. Sound program hearing device settings furthermore may comprise a list of sound processing features. The sound processing features may for example be a noise cancelling algorithm or a beamformer, which strengths can be increased to increase speech intelligibility but with the cost of more and stronger processing artifacts. The operation of each sound program hearing device settings, sound processing features, and parameters related thereto may be adjusted using the methods and apparatuses described herein responsive to user's natural language inputs.

The sound output component 22 generates sound from the modified audio signal and the sound is guided through the tube 18 and the second part 16 into the ear canal of the user. The hearing device 12 may include a control module 44, being a control unit. For instance, the control module 44 may be implemented as a computer program executed by the first processing unit 40. Alternatively, the control module 44 may comprise a control processor implemented in hardware or more specific a DSP (digital signal processor). The control module 44 may be configured for adjusting the parameters of the sound processing module 42, e.g. such that an output volume of the sound signal is adjusted based on an input volume. For example, the user may select a modifier (such as bass, treble, noise suppression, dynamic volume, etc.) and levels and/or values of the modifiers with the input mean 24. From this modifier, an adjustment command may be created and processed as described above and below. In particular, processing parameters may be determined based on the adjustment command and based on this, for example, the frequency dependent gain and the dynamic volume of the sound processing module 42 may be changed.

All these functions may be implemented as different sound programs stored in a first memory 50 of the hearing device 12, which sound programs may be executed, adjusted, etc. by the sound processing module 42. The first memory 50 may be implemented by any suitable type of storage medium, in particular a non-transitory computer-readable medium, and can be configured to maintain, e.g. store, data controlled by the first processing unit 40, in particular data generated, accessed, modified and/or otherwise used by the first processing unit 40. The first memory 50 may also be configured to store instructions for operating the hearing device 12 and/or the user device 14 that can be executed by the first processing unit 40, in particular an algorithm and/or a software that can be accessed and executed by the first processing unit 40.

The first memory 50 of the hearing device 12 may be a part of the memory 130 storing instructions according to the present embodiments and the first processing unit 40 may be a processor 132 of a control system 100 (see FIG. 4), which comprises the hearing system 10. As such, the hearing system 10 determines and monitors the hearing situation of the user (e.g., by the sound detector 20), and those metrics may be used to further determine a context for a user's natural language input so that the system can better determine how to respond to the user and suggest and/or implement a change in settings of the hearing system to help the user resolve an issue or otherwise respond to a user's request.

The hearing device 12 may further comprise a first transceiver 52. The first transceiver 52 may be configured for a wireless data communication with a remote server 72, which may be part of a control system 100 (see FIG. 4) for the hearing system 10. The control system 100 or other functions described herein may be implemented completely within the hearing system 10, i.e. without remote server 72, may be implemented between some combination of the devices of the hearing system 10 and the remote server 72, or may be implemented solely by the remote server 72, in various embodiments.

Additionally or alternatively, the first transceiver 52 may be adapted for a wireless data communication with a second transceiver 64 of the user device 14 and/or a third transceiver 82 of an external device 80. The first and/or the second transceiver 52, 64 each may be, e.g., a Bluetooth™ or a radio frequency identification (RFID) radio chip.

A sound source detector 46 may be implemented in a computer program executed by the first processing unit 40. The sound source detector 46 is configured to determine at least the one sound source from the audio signal. In particular, the sound source detector 46 may be configured to determine a spatial relationship between the hearing device 12 and the corresponding sound source. The spatial relationship may be given by a direction and/or a distance from the hearing device 12 to the corresponding audio source, wherein the audio signal may be a stereo-signal and the direction and/or distance may be determined by different arrival times of the sound waves from one audio source at two different sound detectors 20 of the hearing device 12 and/or a second hearing device 12 worn by the same user. The determinations of the sound source detector 46 (e.g., the direction and/or distance of an audio source form the hearing device 12) may be one or more metrics used by the system to further determine context of a user's natural language input (e.g., the determinations of the sound source detector 46 may be used to partially determine an embedding vector associated with a user's natural language input).

A first classifier 48 may be implemented in a computer program executed by the first processing unit 40. The first classifier 48 can be configured to evaluate the audio signal generated by the sound detector 20. The first classifier 48 may be configured to classify the audio signal generated by the sound detector 20 by assigning the audio signal to a class from a plurality of predetermined classes. The first classifier 48 may be configured to determine a characteristic of the audio signal generated by the sound detector 20, wherein the audio signal is assigned to the class depending on the determined characteristic. For instance, the first classifier 48 may be configured to identify one or more predetermined classification values based on the audio signal from the sound detector 20. The classification may be based on a statistical evaluation of the audio signal and/or a machine learning algorithm that has been trained to classify the ambient sound, e.g. by a training set comprising a huge amount of audio signals and associated classes of the corresponding acoustic environment. So, the machine learning algorithm may be trained with several audio signals of acoustic environments, wherein the corresponding classification is known. The determinations or classifications of the first classifier 48 may serve as one or more metrics used by the system to further determine context of a user's natural language input (e.g., the determinations of the first classifier 48 may be used to partially determine an embedding vector associated with a user's natural language input).

The first classifier 48 may also be configured to identify at least one signal feature in the audio signal generated by the sound detector 20, wherein the characteristic determined from the audio signal corresponds to a presence and/or absence of the signal feature. Exemplary characteristics include, but are not limited to, a mean-squared signal power, a standard deviation of a signal envelope, a mel-frequency cepstrum (MFC), a mel-frequency cepstrum coefficient (MFCC), a delta mel-frequency cepstrum coefficient (delta MFCC), a spectral centroid such as a power spectrum centroid, a standard deviation of the centroid, a spectral entropy such as a power spectrum entropy, a zero crossing rate (ZCR), a standard deviation of the ZCR, a broadband envelope correlation lag and/or peak, and a four-band envelope correlation lag and/or peak. Each of these characteristics or signal features present in an audio signal may also be used as metrics for determining a context of a user's natural language input and an embedding vector associated therewith as described herein. The first classifier 48 may determine such characteristics or metrics from the audio signal using one or more algorithms. Certain determined characteristics determined from the audio signal (or features extracted by an algorithm based on those features) may be indicative of a particular environment of the user (e.g. a noise level, speech level, type of speech, etc.), which may also be used as a metric for determining a context of a user's natural language input and an embedding vector associated therewith as described herein.

The first classifier 48 may be further configured to assign, depending on the determined characteristic or features extracted, an environment of the user or the detected audio signal to one or more classes (e.g., a specific content in the audio signal such as a speaking activity of the user and/or another person, an acoustic environment of the user, low ambient noise, high ambient noise, traffic noise, music, machine noise, babble noise, public area noise, background noise, speech, nonspeech, speech in quiet, speech in babble, speech in noise, speech in loud noise, speech from the user, speech from a significant other, background speech, speech from multiple sources, calm situation, etc.). A determined class assignment(s) of an audio signal or user environment to one or more predetermined classes may be used as metrics for determining a context of a user's natural language input and an embedding vector associated therewith as described herein.

The hearing device 12 may further comprise a first transceiver 52. The first transceiver 52 may be configured for a wireless data communication with the remote server 72. Additionally or alternatively, the first transceiver 52 may be adapted for a wireless data communication with the second transceiver 64 of the user device 14 and/or the third transceiver 82 of the external device 80. The first, second, and/or third transceiver 52, 64, 82 each may support known low power wireless data transmission protocols, e.g., a Bluetooth™ or radio frequency identification (RFID) radio chip.

Each of the sound processing module 42, the control module 44, the sound source detector 46, and the first classifier 48 may be embodied in hardware or software, or in a combination of hardware and software. Further, at least two of the modules 42, 44, 46, 48 may be consolidated in one single module or may be provided as separate modules. The first processing unit 40 may be implemented with a single processor or with a plurality of processors. For instance, the first processing unit 40 may comprise a first processor in which the sound processing module 42 is implemented, and a second processor in which the control module 44 and/or the sound source detector 46 and/or the first classifier 48 are implemented. The first processing unit 40 may further comprise the processor 132 for executing the control system 100 as a further processor. Alternatively the one of first or second processor may be used as processor 132.

The user device 14, which may be connected to the hearing device 12 for data communication, may comprise a second processing unit 60 (e.g., a processor) with a second memory 62, and a second transceiver 64.

The second processing unit 60 may comprise one or more processors, such as CPUs. If the hearing device 12 is controlled via the user device 14, the second processing unit 60 of the user device 14 may be seen at least in part as a controller of the hearing device 12. In other words, according to some embodiments, the first processing unit 40 of the hearing device 12 and the second processing unit 60 of the user device 14 may form the controller of the hearing device 12. A processing unit of the hearing system 10 may comprise the first processing unit 40, the second processing unit 60, and/or a third processing unit 84 (e.g., a processor) of the external device 80. Thus, first, second, and/or third processing units 40, 60, 84 may therefore form the processor 132 in various embodiments. In other words, a processor as used herein may be any one of or any combination of the processors or processing units described herein (e.g., 40, 60, 84, and/or 132). As such, a processor may be distributed such that the various operations described herein may be carried out by one processor or multiple processors together (e.g., the processor is formed of individual processor units) that are able to communicate and synchronize with each other to accomplish various tasks or execute various instructions together.

The second processing unit 60 and the second memory 62 may be alternatively processor 132 and memory 130 according to the present invention. In particular the database 140 may be stored in the second memory 62.

The hearing device 12 and the user device 14 and in particular the processing units 40, 60 may communicate data via the first and second transceivers 52, 64, which may be Bluetooth™ transceivers. The hearing device 12 and the user device 14 may be connected for data communication via a wireless data communication connection.

With the hearing system 10 it is possible that the above-mentioned modifiers and their levels and/or values are adjusted with the user device 14 and/or that an adjustment command is generated with the user device 14 and sent to the hearing device 12. This may be performed with a computer program run in the second processing unit 60 and stored in the second memory 62 of the user device 14. This computer program may also provide the graphical user interface 32 on the display 30 of the user device 14. For example, for adjusting the modifier, such as volume, the graphical user interface 32 may comprise the control element 34, such as a slider. When the user adjusts the slider, an adjustment command may be generated, which will change the sound processing of the hearing device 12. Alternatively or additionally, the user may adjust the modifier with the hearing device 12 itself, for example via the input mean 24.

The hearing device 12 and/or the user device 14 may communicate with each other and/or with the remote server 72 via the Internet 70. The method explained below may be carried out at least in part by the remote server 72. For example, processing tasks, which require a huge amount of processing resources, may be outsourced from the hearing device 12 and/or the user device of 14 to the remote server 72. Further, the processing units (not shown) of the remote server 72 may be used at least in part as the controller for controlling the hearing device 12 and/or the use device 14. Thus, the processor 132 for executing the control system 100 of the hearing system 10 as well as the memory 130 may be at least partially located on the remote server 72.

The user device 14 may comprise a further module 68 that may be or may function similarly to any or all of the sound processing module 42, the control module 44, the sound source detector 46 of the hearing device 12.

The user device 14 may comprise a second classifier 66 that may have the same functionality as the first classifier 48 explained above and/or also may be based on a machine learning algorithm. The second classifier 66 may be arranged alternatively or additionally to the first classifier 48 of the hearing device 12. The second classifier 66 may be configured to classify the acoustic environment of the user and the user device 14 depending on the received audio signal, as explained above with respect to the first classifier 48, wherein the acoustic environment of the user and the user device 14 corresponds to the acoustic environment of the hearing device 12 and wherein the audio signal may be forwarded from the hearing device 12 to the user device 14. The system as explained here may thus comprise a certain number of classifiers, for example classifying movement, time, noise, environment for describing the possible hearing situations of the user.

The external device 80 may be or may comprise, e.g., a television connector or television, a sound system connector or a sound system, a Roger™ wireless microphone, etc. As such, the external device 80 may include a sound detector 90 (e.g., a microphone) that detects sound signals, which may be processed by any of the first, second, and/or third processing units 40, 60, 84 and/or the processor 132 of FIG. 4. Such sound signals or characteristics or classifications determined therefrom may be used as metrics for processing a natural language input from a user as described herein. Further, settings of the external device 80 and/or the mere presence of or connection to the external device 80 to the user device 14 and/or the hearing device 12 may be used as a setting of the hearing system for processing a natural language input from a user as described herein.

The external device 80 may be connected to or be part of a sound system (e.g., at a public event such as a speech, church service, concert), television, or other device so that sound detected by or processed by the external device 80 may be transmitted from the external device 80 to any of the hearing device 12, the user device 14, and/or the remote server 72. For example, sound detected by and/or processed by the external device 80 may be transmitted directly to the hearing device 12 to assist the user in hearing the sound system, television, etc. Similarly, the external device 80 may be a portable microphone device configured to be placed near a human speaker or source of sound to assist in capturing audio from significant distances for transmission to any of the hearing device 12, the user device 14, and/or the remote server 72. As with the hearing device 12 and the user device 14, settings of the external device 80 and metrics collected by and/or measured by the external device 80 may be used to determine vector embeddings related to a user's natural language input, such that a system can use additional information from the external device 80 to contextualize a user's request and provide a useful response as described herein.

Various functions of measuring metrics, collecting and/or processing sound signals, and any of the other methods described herein may be implemented as programs or instructions stored in whole or in part in a third memory 88 of the external device 80, which programs and instructions may be executed, adjusted, etc. by a sound processing module 86 (e.g., a processor) of the third processing unit 84. The third memory 88 may be implemented by any suitable type of storage medium, in particular a non-transitory computer-readable medium, and can be configured to maintain, e.g. store, data controlled by the first external device 80, in particular data generated, accessed, modified and/or otherwise used by the third processing unit 84. The third memory 88 may also be configured to store instructions for, in part or in whole, operating the hearing device 12 and/or the user device 14 and implementing the various methods for processing natural language inputs from a user that are described herein as being executed by any of the first processing unit 40, the second processing unit 60, and/or the remote server 72. That is, the methods described herein may be implemented by any one of, or any combination of, the hearing device 12, the user device 14, the external device 80, and/or the remote server 72.

Figure 3:
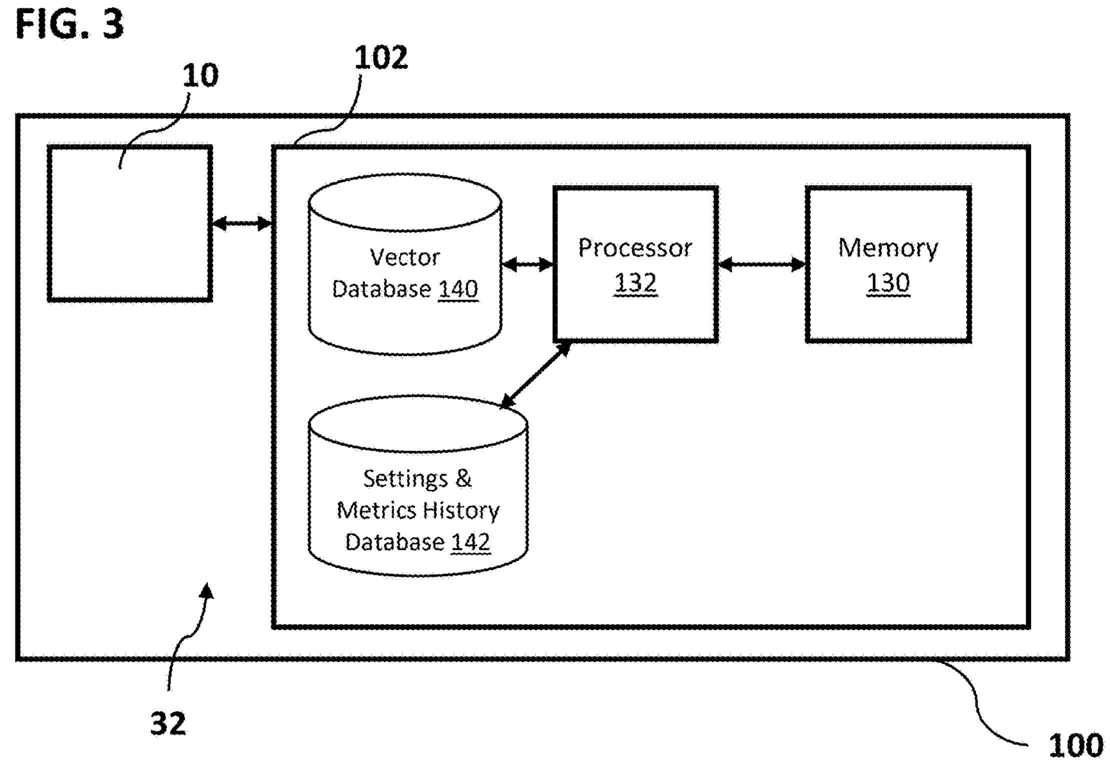
FIG. 3 schematically illustrates a control system of the hearing system according to FIG. 1.

The control system 100 is described with respect to FIG. 3. It is shown that the control system comprises the hearing system 10 and a part 102 in addition to the hearing system 10, such as the remote server 72 that may include a vector database 140 and a settings and metrics history database 142. The settings and metrics database may be used to provide information related to historical settings and metrics (e.g., 416 of FIG. 4) to a fitting GPT (e.g., 402 of FIG. 4) for consideration in generating embedding vectors related to a problem or issue faced by a user. For example, the settings and metrics database 142 may include settings/metrics history relating to how devices have been configured in the past, what metrics were present during those past settings/configurations, whether certain configurations in the past were based on recommendations from the system, whether the user indicated that the settings or setting changes recommended by the system were effective in addressing the issue, etc. In this way, various information related to historical settings/metrics and efficacy of historical settings may be stored in the settings and metrics database 142 and used to find possible solutions to a user's issue(s).

The remote part 102 is depicted abstractly, solely showing that it comprises one or more computing devices with at least one processor 132, at least one memory 130 and at least one database 140, 142. FIG. 3 also shows that the components of the remote part 102 are in data communication with each other and the hearing system 10. While the example of FIG. 3 shows the components of the remote part 102 as being separate from the components of the hearing system 10 (e.g., where the remote part 102 is part of one or more remote servers such as the remote server 72), in various embodiments some or all of the components of the remote part 102 may be part of one or more of the external device 80, the hearing device 12, and/or the user device 14 of the hearing system 10. That is, the various components and their associated functions and methods may be implemented by different combinations of the various devices and components shown in the figures and described herein.

As such, the various embodiments described herein may be used with respect to the components shown in and described with respect to FIGS. 1-3. Users who wear such hearing devices may benefit from fine adjustments to their hearing devices or other devices that they use. For example, adjustments of a hearing or other device may be to an applied gain, sound cleaning features, and other controls. Such adjustments may depend on, for example, (i) a specific situation the end user is in (e.g., a classification) which may be measured or determined based on metrics collected by various devices as described herein, (ii) various settings of the devices used in a given hearing system by a user, (iii) the types of devices currently in use or attempted to be in use by a user in the specific situation (e.g., the type of device and its connectivity status/setting). These factors make for a complex problem with many dimensions for determining the best settings, fittings, devices, etc. for a user that is subjected to dynamic situations, and in such situations the users may or may not have a full complement of their devices available for use at any given time (e.g., the user may not have an external device such as a portable microphone readily available in certain situations, the user may not have a hearing aid accessory or fitting that would be optimal for a given situation).

To find an optimal adjustment that meets the needs of the end user, a hearing care professional (HCP) typically conducts speech recognition tests and adjusts the fitting and hearing device settings accordingly. However, the effectiveness of this approach may be limited due to the artificial nature of such tests and the limited time the HCP has with the end user. If a problem arises in a real-life situation, the HCP may not be present to address it, and the problem may be resolved during a later session with the HCP, making it challenging to find a proper solution since the user may no longer be in that real-life situation when they visit the HCP. Furthermore, the more time that passes between a real-life experience of an end user and a visit with an HCP, the more recall bias may play a role in the end user's recall of issues with their hearing device.

However, existing capabilities of applications (apps) used to solve specific user problems or issues remain limited (e.g., the options available for selection may not solve the problem or issue faced by the user, a user may not be able to find a correct option for addressing their issue even if they attempt to do so in the app, the user may not utilize the options available), such that users may often not be able to solve an issue faced in a real-world situation, making it difficult to hear, communicate, etc. despite using a hearing device. As a result, the fitting parameter set of a hearing device and the hearing device settings may often be in a suboptimal state for a user. As such, described herein is a tool available to an end user to input natural language inputs describing their issue or request (e.g., allow the user to input text or speech freeform without having to search through available menu options), and returning suggestions or instructions for modifying certain settings related to a hearing device, user device, and/or external device within an application (or app) running on a user device (e.g., a user's smartphone, laptop, tablet). In various embodiments, the tool may also be able to automatically update or change a setting based on the suggestion of the system without requiring the user to navigate to or specifically change a given setting on a user device.

The solutions provided herein use, for example, a large language model (LLM), such as a fine-tuned LLM, to determine an issue or other request made by a user based on a user's natural language input (e.g., into a user device via speech or text), so that the user may no longer need to use an expert fitting companion or HCP that helps the end-user to reach, activate, and adjust the settings that may be used to optimize personalized hearing. The LLM may be fine-tuned, instruction-tuned, generic and prompt engineered, or any combination thereof. As such, a user may input a textual or speech-based natural language input, and that natural language input may be used and processed by an LLM as described herein to create an output (e.g., a recommended setting adjustment for a hearing device, recommended external device to use, recommended configuration or setting for an external device, recommendation for a fitting parameter set of a hearing device, etc.) based on natural language input.

Inputs used to determine an output for the user may include, for example, (i) free text about the issue (e.g., "I have trouble understanding people"), (ii) temporal information about their issue (e.g., issue is being experienced right now, issue was experienced at some point in the past), (iii) hearing device metrics (e.g., signal level, noise floor estimation, signal-to-noise ratio, classified sound sources, estimated listening intention etc.), (iv) hearing device configuration/settings (hearing aid type, coupling, feedback threshold, real ear transfer functions ear-to-coupler level difference (ECLD), real-ear unaided gain (REUG), real-ear occluded gain (REOG), target gain, actual gain, actuator settings, actual feedback stability, hardware test parameter(s), etc.). Each of these inputs may be related to one or more dimension used to generate an embedding vector that takes into account a plurality of different types of inputs.

Example outputs of the systems and methods described herein based on a natural language input from a user may generally include (i) a most probable solution to the problem based on an embedding vector-database lookup, (ii) follow-up question(s) to the user to increase match to specific problems in the vector-database, (iii) gain/actuator adjustments or adjustments to any other setting, (iv) instructions for using or adjusting a hearing device, a user device, and/or external device, and/or (v) follow-up question(s) to the user to determine if the recommended solution worked for the user to solve their issue and/or answer their request.

The embodiments herein therefore provide for an interface of a user device (e.g., the user device 14) so that the user can name or describe a problem in a natural language input (e.g., using free text entered by a user such as through a keyboard of a user device, using spoken words that are detected by a microphone and converted to text, using motion sensing or visual sensors to detect sign language inputs that may be converted to text, etc.). For example, the natural language input may be similar in content to how a problem or issue of a user would be described/stated to an HCP, except that the current embodiments allow a user to input a request at any time and situation. Such a system solves technical problems where a user cannot adequately configure the devices of their hearing system on their own and where even an HCP may not be able to fully appreciate a given situation or issue a user is facing to make adjustments, as the user may often see the HCP after the user is no longer in that situation or facing that issue.

An example interaction between a user and an LLM of a fitting generative pre-trained transformer (GPT) is shown in and discussed below with respect to FIG. 5 below. Depending on if the situation occurred in the past or at the current time, the LLM may map the natural language input and hearing aid over the last X minutes (if the issue was experienced at the current situation) to a latent representation (text embedding) using a text encoder (e.g., 408 of FIG. 4). This embedding can then be searched in a problem vector-database (e.g., 140 of FIG. 3, 410 of FIGS. 4 and 5). The database contains tuples of text embeddings (vectors) of problems with one or more known related solutions (e.g. for the embedding of "I have problems understanding speech" a known solution is to increase gain by a particular decibel (dB) level in the frequency range relevant to speech). The search provides a probability of a match towards any problem in the database. This probability is based on the distance metric between the calculated embedding vector (e.g., 424 in FIG. 4) and the embedding vectors (e.g., 426 in FIG. 4) in the database. If the probability score is above a predetermined threshold, a corresponding gain correction would be applied and/or the user is presented with the option to adopt the corresponding gain correction recommended by the system.

Embedding vectors in the database may also be combinations or ordered combinations (e.g., tuples) of embedding vectors combined into a single embedding vector. The combined embedding vector of the stated issue by the user is compared against all various combinations of embedding vectors stored in the database. In a case where an issue embedding vector matches the embedding vector representative of a combination of two or more embedding vectors, the proposed solution may also be related to the combination or tuple of those vectors that are combined to yield a single combined embedding vector. For example, if the user describes an issue which corresponds to an embedding vector that is similar to the combination of two embedding vectors in the database (e.g., (1) reverberation in speech in noise situation and (2) overall too loud in speech in noise situation), a mixture of the respective gain corrections in the problem/solution tuple database is applied or recommended to the user.

In other embodiments, the two embedding vectors may be stored individually as embedding vectors in the database as tuples with their related solutions, but a tuple including a third embedding vector that represents a combination of the two embedding directors may be stored along with a related solution for that third embedding vector. In various embodiments, the combined embedding vector in this manner may be ordered or not ordered. For example, a non-ordered combined embedding vector would be a match regardless of what order the two original embedding vectors representing different issues are in.

In other embodiments, the combined embedding vector may be ordered, such that the same two original embedding vectors may be stored as two different combined vectors having different ordered combinations, which may each also be stored with a different related solution based on the order of the combined vectors. Such combined vectors may be useful where the order may indicate that a different solution to be proposed, such as if the user raises a first issue in a first natural language input and raises a second issue in a second natural language input response to a follow-up question from the system. In such an instance, the order in which the user entered the issues may be significant for determining the most applicable solution for the user (e.g., the first issue may be more important that second issue is relevant but secondary to the user's concern/issue). For example, if an initial probability score after a first natural language input is below a certain threshold, a follow up question is asked to the end user (e.g., the original issue "overall too loud" would cause the follow up question by the LLM block: "Does this issue apply to any situation or only specific situations, such as when in a restaurant?"). This process may be repeated a predetermined number of times (after which the best solution may be proposed to the user even if it does not reach the predetermined threshold) or until the threshold is reached. As such, any number of embedding vectors may be determined and combined to generate an embedding vector for comparison to the tuples (e.g., embedding vectors/related solution combinations) in the vector database.

The above example relates to a gain correction, but as described herein various types of outputs may be the recommendation or solution provided to the user. For example, recommendations/solutions may also be related to any actuators of a hearing device, fitting adjustments, etc. For example, an issue with understanding speech in noise could be remedied with a corresponding beamformer strength increase, denoising strength increase, etc., which may be represented in the vector database. Such adjustments can be of permanent nature (e.g., permanent gain change to a specific set of programs) or temporary (e.g., activate manual programs or automatic mode, volume control, other available macro control, automatic behavior, make a change to a setting for a predetermined amount of time, make change to a setting until a device of the hearing system detects that the conditions/metrics present while the user had the issue are no longer present). Such settings for inputs and for solution outputs may also relate to various types of external devices that may be used in a hearing system (e.g., a solution may be to activate or adjust a setting of a television or television connector, a Roger™ microphone, etc.).

The system may also be configured to return suggestions to a user about hardware changes, such as those related to a coupling of a hearing device. For example, if a user is fitted with an open dome, where a) the sound cleaning features are less performant and b) gain is limited due to feedback threshold, the model may ask the user if a hardware change is possible and if so, provide a corresponding suggestion to change to a different piece of hardware/fitting (e.g., to a vented dome).

The system may also be configured to return instructions and/or educational information to the end user, such as cleaning instructions; how to insert the hearing device; how to order spare/additional parts; how to contact an HCP; suggest information/material/apps to help with tinnitus, cognitive training, coping strategies, communication strategies (e.g., provide a suggestion to move closer to a speaker, turn off radio, close window when noise is coming from outside), etc.; how to use speech to text or translation tools; etc.

Where an appointment with an HCP is desired by the user and/or recommended by the system, one of the devices (e.g., the user device) may also be used to schedule an appointment with the HCP, initiate a voice or video call to the HCP, etc. For example, this can be either the organization of a physical appointment with the HCP or via establishing a remote session within an app operating on the user device. The HCP interfacing could comprise providing all the gathered information of the model to the HCP (e.g. what has been tried/adapted/reverted, etc.). This may make the HCP more efficient and better able to identify a solution for the user. As referred to herein, an HCP may also at times be a user of the system. That is, not only an end user needs to input natural language inputs and receive solutions to issues related to those natural language inputs. Instead, a user may be an end user, an HCP, or anyone else that inputs natural language inputs to seek a solution for an issue with a hearing system (e.g., a relative of an end user of a hearing device).

Because some solutions might not always be applicable, the problem/related solution tuples in the vector-database may be pre-filtered prior to searching for a match based on a hearing device being used, current or available hearing device settings, an external device being used, and/or current or available external device settings. For example, if a user is already using a Roger™ microphone, tuples having a solution that suggests that a user start using a Roger™ microphone may be eliminated prior to performing more costly processing of comparing numerous vectors with one another to find a match. That is, eliminating certain tuples from the vector database as a possible solution may advantageously allow the system to not have to compare every single embedding vector of every single tuple in the vector database to the embedding vector generated based on the user's natural language input. This may advantageously preserve computing resources, return a better solution to the user in less time, etc. As another example, if a user is using a custom shell with a hearing device, solutions related to changing/substituting the dome would not be applicable useful solutions. As another example, if a hearing device does not support activation of a specific program, solutions related to that program may be eliminated as possible solutions to the user's issue. As another example, if a feature or setting is already at a maximum setting level, then solutions related to increasing the setting level for that particular setting may be eliminated. As such, settings of devices, presence of devices, status of devices (are they connected to the hearing device, are they being used), metrics measured by the devices, etc. may all be used to rule out or pre-filter tuples from the vector database based on the solutions in those tuples, prior to performing costly comparisons between vectors. In various embodiments, rather than pre-filtering prior to matching the embedding vectors as described, a similar effect may be achieved by encoding of the user interaction together with the hearing and/or external device settings and/or metrics, such that the generated embedding vectors will not align.

The embodiments herein also include reverting to the changes made based on an interaction with the user in various situations. For example, if a similar acoustical situation or one or more measured metrics are detected to what has been previously detected or a natural language input is received from a user that is similar to one previously received, the system may implement changes or solutions that are the same as or similar to what was implemented in the previous similar situation. Similarly, the system may also revert back to an original state (e.g., before the change or solution was implemented) when the similar acoustical situation or one or more measured metrics are no longer present. In various embodiments, the system may also present the user with follow up questions at some time after implementing the change (e.g., immediately after, after a predetermined amount of time such as a minute, five minutes, fifteen minutes, thirty minutes, one hour, two hours, four hours, six hours, twelve hours, eighteen hours, one day, two days, four days, one week, etc.) to ask the user if the applied solution or correction has helped to remedy the problem, either completely or in part. Those applied solutions and their respective embedding vector in the tuples may be supplemented with quality labels based on the user responses. The tuples in a vector database may be modified based on the user responses (e.g., where a correction did not solve the user's issue). The feedback may also be used to modify how similarity scoring between vectors is calculated, may be used to adjusted weights of a text encoder used to encode natural language inputs from a user, etc. As such, the user feedback may be used to continuously improve the vector database and/or the algorithms used to determine similarity scores when comparing vector embeddings to determine a possible related solution to an issue faced by a user.

A possible solution (and/or its related embedding vector) may also undergo one or more post-processing steps prior to providing the recommended solution to the user and/or implementing a setting change based on the solution. For example, a post-processing step to ensure safety-related constraints may be applied (e.g., only recommend a setting change for gain as long as maximum gain limitations are not exceeded). Another post-processing step may occur to ensure that a setting change will be of a minimum magnitude. For example, small changes may be so small such that they are imperceptible to a user and therefore may not be useful in addressing a concern or request of a user. As such, the system may process a possible solution to ensure that the recommended solution is of a minimum predetermined magnitude for a particular setting such that it is useful to the user. In some embodiments, if a given setting change of a possible solution is below a minimum predetermined magnitude, the system may also optionally omit the setting change from the recommended solution as opposed to increasing a magnitude of the recommended setting change to a level at or above the minimum predetermined magnitude.

The encoding of the natural language input together with, hearing device settings and/or metrics, external device settings and/or metrics, etc. into a single embedding (e.g., based on an ordered combination of those items or a non-ordered combination) may be, for instance, achieved by collecting all parameters and settings in a structured dictionary including the user's natural language input/conversation. For example, parameters assembled by an encoder for creation of an embedding vector that represents a combination of available settings, multiple natural language inputs from the user, etc., may be:

```
{
  "Available Programs": ["SpeechInQuiet", "SpeechIn-
    Noise"],
  "Beamformer Strengths per Program": [0.2, 0.8]
  . . .
  "Conversation": "U: 'I have problems understanding
    speech.'; FGPT: 'In which situation does this occur';
    U: 'In restaurants' [End]"
}
```

In various embodiments, the system may also identify a direct solution (e.g., where a user request is directly related to a particular solution, where the user request does not require acting on any hearing or external device settings, etc.), and therefore the system may return an answer without having to generate embeddings, embedding vectors, and compare against a vector database to find a solution (e.g., where a user input is "increase gain" the system may recognize the instruction and increase gain of a user's hearing device. In other embodiments, the system may identify the text as pertaining to an unrelated problem (e.g., a random input, "the sky is blue"), and therefore may ignore the input or return a default message (e.g., a message asking the user to try again) without generating embedding vectors or performing embedding vector comparisons.

Various example embodiments are further described herein. However, it should be noted that some of these examples are simplified for ease of understanding of the reader and ease of presenting the figures. For example, in FIG. 6, tuples representative of embedding vectors having two dimensions (e.g., representing environmental inputs speech and noise) and pointing to a particular related solution are shown. A user natural language input of "I do not understand speech in a restaurant" would align with both dimensions, hence possible solutions shown in FIG. 6 include increasing beamformer strength, increasing gain, and increasing denoising. Each related solution (or a combination of related solutions where an embedding vector falls somewhere between one of the vectors in FIG. 6) could be suggested to the user and applied to hearing device settings. As another example, if a user expressed an issue that "Everything is too loud when being outside in traffic without having a conversation," an embedding vector based on that natural language input may align with the combination negative "increase gain" (i.e. decrease gain) and increase denoising. However, these examples only relate to two dimensions. In practice, an embedding vector-space used in the embodiments herein may be learned (e.g., the fitting GPT learns the dimensions) and the dimensions may numerous (e.g., in the tens, in the hundreds, etc.).

Figure 4:
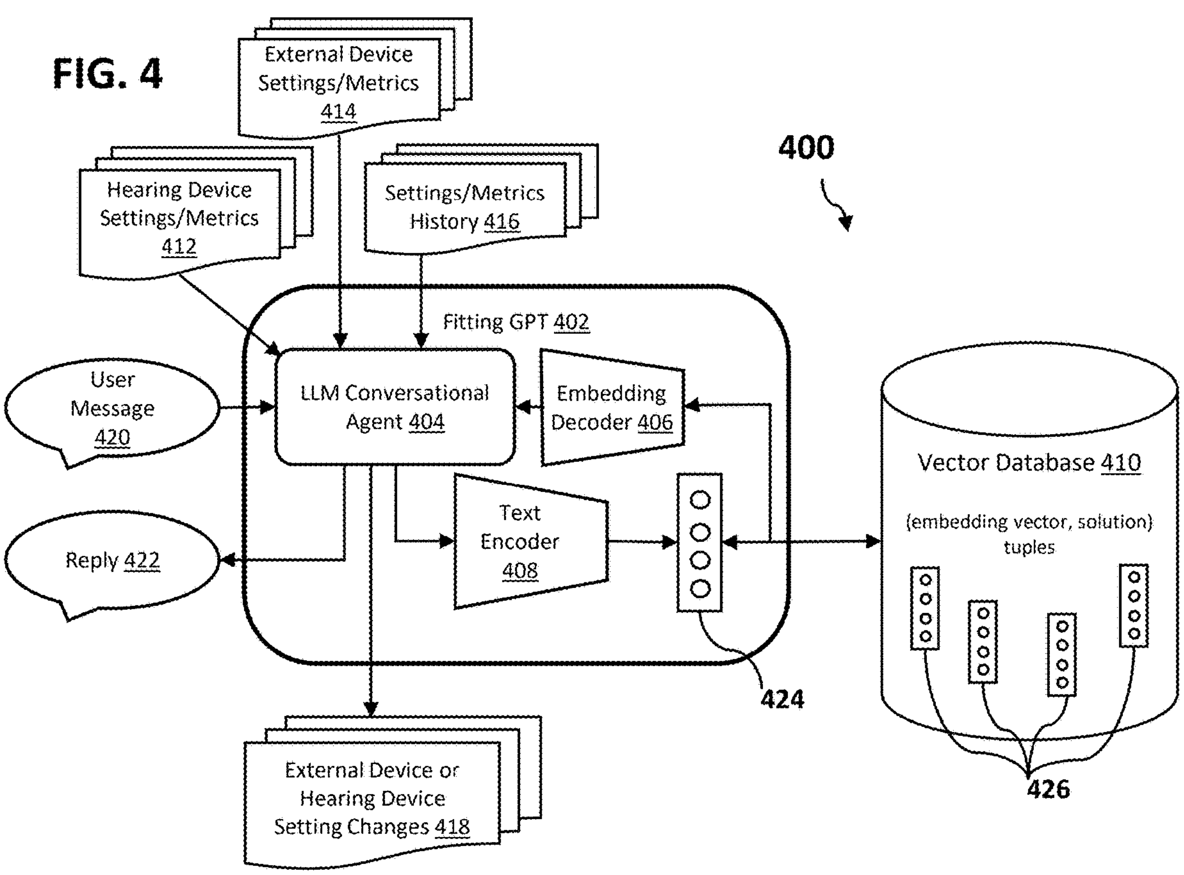
FIG. 4 schematically illustrates components of a hearing system for generating embeddings of natural language inputs from a user and determining solutions for issues related to the natural language inputs.

FIG. 4 schematically illustrates components 400 of a hearing system for generating embeddings of natural language inputs from a user and determining related solutions for issues related to the natural language inputs. In particular, a fitting GPT 402 includes an LLM conversational agent 404 configured to receive messages, such as the user message 420, in natural language and respond in natural language to a user, as in reply 422. The LLM conversational agent 404 further may receive additional text inputs related to a hearing device settings and/or metrics 412, an external device settings and/or metrics 414, and/or settings and metrics history 416. The fitting GPT 402 may assemble all available information (e.g., 412, 414, 416, 420) and send it to a text encoder 408 configured to determine embeddings for the available information (e.g., 412, 414, 416, 420). Such embeddings may each represent a dimension of a vector, and therefore a vector embedding 424 may be generated based on the embeddings from the text encoder 408.

The fitting GPT 402 may then compare the vector embedding 424 to tuples 426 stored in a vector database 410. Each of the tuples 426 in the vector database 410 include a vector embedding and a related solution associated with that vector embedding. As such, the fitting GPT 402 may be configured to find the closest fit or match between the embedding vector 424 and the embedding vectors of the tuples 426. As described herein, a closest fit or match may occur when the embedding vector 424 has a similarly score above a predetermined threshold as compared to an embedding vector of a tuple 426 in the vector database 410.

In various implementations, some or all of the plurality of tuples 426 may be manually defined by a user based on previously identified problems with hearing devices and those identified problems' respective or associated related solutions. That is, the embedding vectors may be manually defined by a user to seed the vector database, and the related solutions associated with specific embedding vectors may additionally be manually defined and linked to particular embedding vectors in the vector database 410.

Once one of the tuples 426 is identified as being a closest match to the embedding vector 424, that selected tuple 426 is decoded by an embedding decoder 406 to decode information about the embedding vector and related solution of the selected tuple. That decoded information may be used by the LLM conversational agent to return the reply 422 to the user and output information for an external or hearing device setting change 418 (e.g., to change how the hearing device of a user operates to attempt to solve the issue faced by the user).

As such, herein is described a solution with a fine-tuned LLM approach. However, other types of LLMs and LLM formation and trainings are contemplated herein. For example, an LLM may also be instruction-tuned, or may be generic and prompt engineered only. In various implementations, more than one type of formation and/or training may be used (e.g., fine-tuned, instruction-tuned, generic and prompt engineered).

In various implementations, each time a user accepts or rejects a suggested setting, that response from a user may also serve as implicit feedback to further train and/or refine the LLM, redefine embedding vectors, adjust weights in the text encoder and/or embedding decoder 406, etc. As such, pre-existing solutions and newly generated solutions in a vector database may be linked to pre-existing and/or new problem descriptions, thus creating an ever expanding problem/solution pool in the vector database 410. Such additional information may be advantageous for enhanced vector similarity scoring and/or for reinforcement of the model.

FIG. 5 schematically illustrates an example flow 500 of messaging between a user 504 (and/or their user device) and the fitting GPT 402 of a hearing system. First, the user may input a message 502 indicating a problem understanding speech. The message 502 may be input into the fitting GPT 402, and the fitting GPT 402 may determine whether there is a match in the vector database 410. In this instance, no match that was close enough is found, so the fitting GPT 402 outputs a message 506 indicating as such and asking the user for more information about the problem to be included in the embedding vector that is representative of the user's issue (e.g., the message 506 includes a follow-up request).

The user answers with a message 508 indicating that the user is experiencing the issue in restaurants (e.g., the message 508 represents a follow-up answer to the follow-up request in the message 506). The fitting GPT 402 then finds a match with a tuple in the vector database 410 and returns a message 510 indicating the match and proposing a possible related solution to implement a proposed setting change 418 to the user 504. With a message 512, the user assents to the proposed possible solution and implementation of the setting change 418 (e.g., the message 512 includes a confirmatory response to a reply output of the message 510).

The fitting GPT 402 further outputs a message 514 indicating that the setting has been updated and requesting whether the setting change 418 worked to address the user's issue (e.g., the message 514 includes a request to confirm an efficacy of the setting change 418). A confirmatory response in message 516 from the user 504 indicates that the user believes their issue has been addressed. That confirmatory response may be used to validate vectors in the vector database, add a new vector, revise a vector, etc. so that the system may continue to learn and better find matches between vectors representative of users' problems and vectors associated with related solutions to those problems.

Figure 6:
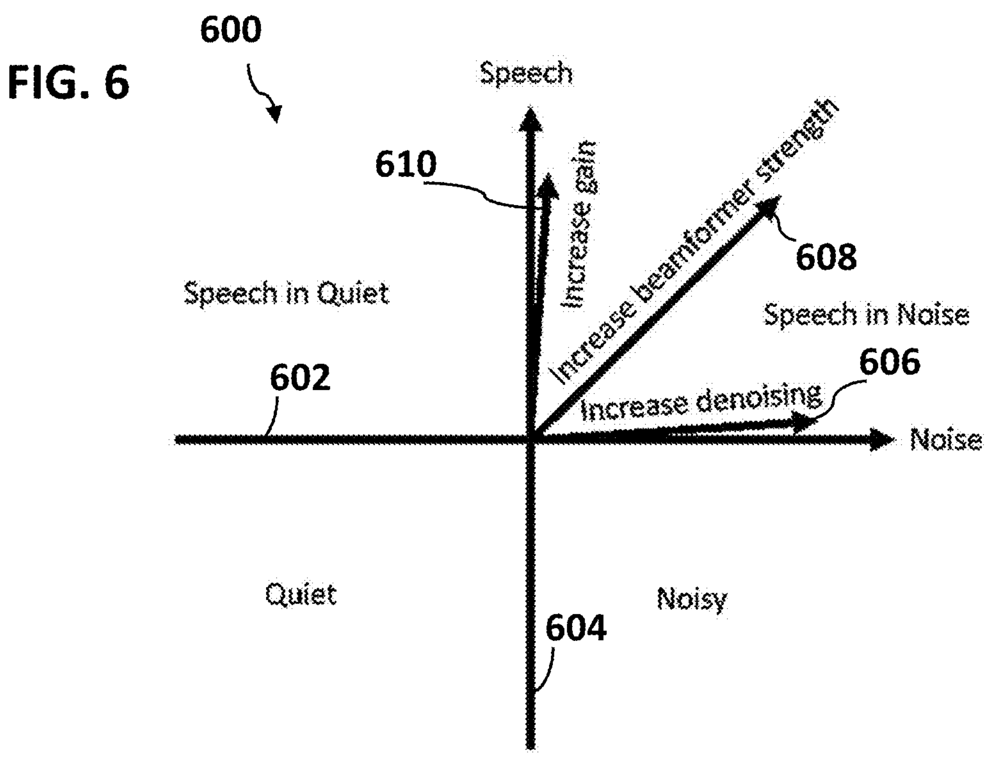
FIG. 6 graphically illustrates dimensions of vector embeddings and solutions relating to particular vectors for a hearing system.

FIG. 6 graphically illustrates dimensions 602 and 604 of vector embeddings 606, 608, and 610 and solutions relating to those vectors 606, 608, and 610 for a hearing system. As described herein, FIG. 6 represents two dimensions that may be used to define vectors (e.g., speech and noise), but in various embodiments many additional and different dimensions may also be used to define vectors. In the particular example of FIG. 6, the vectors shown relate to embeddings that may be generated by a text encoder relating to noise levels and speech levels. Those embeddings may be used to generate or represent vectors, where examples are shown in FIG. 6 as vectors 606, 608, and 610. Each vector 606, 608, and 610 is further associated with a possible related solution (e.g., increase denoising, increase beamformer strength, increase gain, respectively) to form a tuple that may be stored in a vector database. These tuples and vectors may be used to determine a match to an embedding vector that is representative of a user issue as determined from a natural language input from a user.

Figure 7:
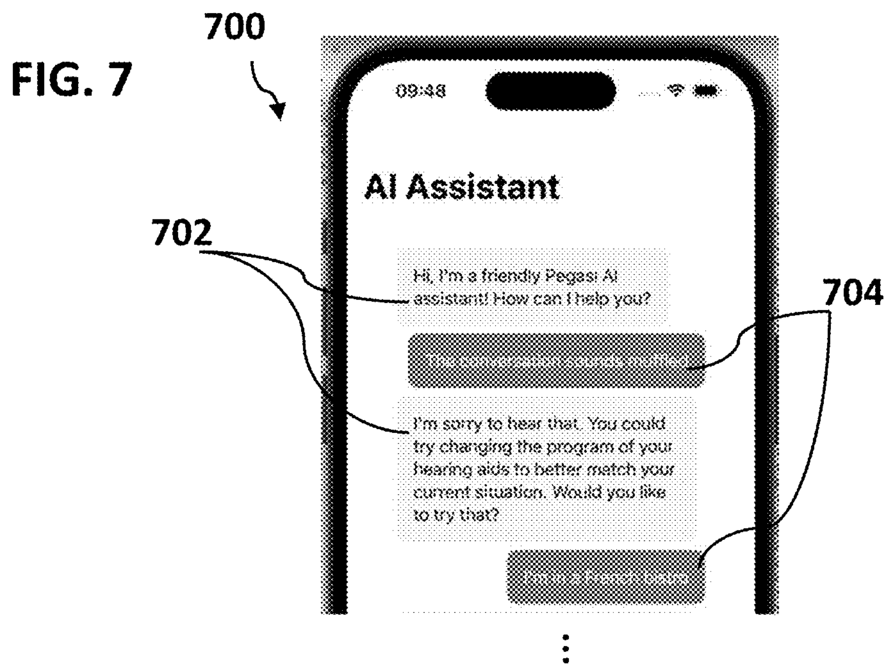
FIG. 7 illustrates an example user interface for a user to enter natural language inputs into a user device.

FIG. 7 illustrates an example user interface 700 for a user to enter natural language inputs 704 into a user device. The user interface 700 may further display responses 702 from a fitting GPT. The communications from the fitting GPT are configured to interact with the end user in a non-technical manner (e.g., mentioning phrases "I'm sorry to hear that. You could try . . . " and the like).

FIG. 8 schematically illustrates a flow chart 800 for processing natural language inputs from a user to determine a related solution to a possible issue related to the natural language inputs. At an operation 802, the method includes receiving, via a user interface, a first signal indicative of a natural language input. The natural language input is indicative of an issue experienced by a user. The issue may be with various different computing devices, such as a hearing device, a user device, an external device, etc. as described herein. The natural language input may include one of text entered by a user through a keyboard of a user interface, speech spoken by the user and sensed by a microphone, gestures of a user detected by a computing device, etc. The natural language input may also include temporal information related to the issue experienced by the user, such as temporal information indicating whether the issue is being currently experienced or was previously experienced by the user, how long ago the issue was experienced by the user, etc.

At an operation 804, a first embedding based on the natural language input is determined. Although a first embedding is described here, in various embodiments the natural language input may include enough information such that more than one embedding is generated from a first natural language input from a user. In such embodiments, each of the embeddings determined by the system may be used for generating an embedding vector (e.g., at an operation 812), such that all information deemed relevant by the system from the natural language input of the user is taken into account in the generation of embedding vectors.

At an operation 806, settings of a hearing and/or external device and/or metrics of a hearing and/or external device are received. These settings and/or metrics may also be used to determine additional embeddings at an operation 808. The settings may include one or more of a fitting parameter set of a hearing device, a type of the hearing device, a coupling setting or type of the hearing device, a feedback threshold of the hearing device, a real ear transfer function setting of the hearing device, a target gain of the hearing device, actual gain of the hearing device, an actuator setting of the hearing device, actual feedback stability of the hearing device, or a hardware test parameter of the hearing device. The metrics may include one or more of a metric measured by a user device, hearing device, and/or external device, such as one or more of a signal level, a noise floor estimation, a signal-to-noise ratio, a classification of a sound source, or an estimated listening intention.

At an operation 810, based on the generated embeddings for the natural language input and any settings or metrics, a first embedding vector. At an operation 812, a closest match is determined between the first embedding vector and one of a plurality of embedding vectors of a plurality of tuples. Each of the tuples include an embedding vector and a related solution for a possible issue experienced by the user.

At an operation 814, a reply is sent to a user interface, where the reply includes information related to a possible solution for the issue of the user. Information in the reply could include information related to a setting change, an instruction to a user to change or add device or accessory in use, instructions for connectivity issues, etc. as described herein.

In various implementations, the system may send, prior to sending the reply output, a follow-up request to the user interface. The follow-up request may request more information related to the issue experienced by the user because the system may not yet have identified a vector embedding in the vector database that is similar enough to the vector embedding generated by the system based on the issue of the user. The system may further receive a follow-up answer to the follow-up request including more information from the user. The system may repeat this process to acquire more information about the user's issue to use for determining embeddings and generating embedding vectors for comparison to the vector database as described herein. In such implementations where a follow-up request is answered, the follow-up request and/or the follow-up answer may also be used to generate the first embedding vector for comparison to the vector database. For example, follow up requests and/or their answers may be taken in an order they were received (or in a non-ordered combination) to generate embeddings and a resulting embedding vector. For example, considering the embodiment in FIG. 5, embeddings for each of the messages 506, 508, and 510 may be determined and then used to generate a vector embedding. That vector embedding may then be used to find a solution to the user's current issue and for saving to update the fitting GPT (and its weights) and the vector database to further enhance the system. For example, in a future request, a user may input a message similar to message 502 of FIG. 5. Instead of asking for follow-up information in message 506, the system may skip to proposing a solution in the message 510 directly responsive to the message 502 based on the system learning from the sequence of messages previously exchanged as shown in FIG. 5 (e.g., the system may infer the follow-up information based on how the initial request is constructed). This may further enhance the system to provide better and faster solutions to a user while minimizing the back and forth messages between the system and the user.

At an operation 814, a reply output is sent to the user interface that includes information related to the solution for the possible issue of the tuple identified from the plurality of tuples stored in the vector database. That is, the system sends information not the user based on the closest solution to the user's issue. As discussed herein, the system may also optionally implement a setting change suggested by the solution, either with or without the user's assent to do so. In other words, the system may receive a confirmatory response from a user device indicating user assent to implementing the solution. In such an embodiment, the system may then implement the solution based on the confirmatory response from the user device. In addition, as shown in FIG. 5, the system may further send a request to the user asking the user to confirm an efficacy of the solution, and the user device may further be used by the user to send back a confirmatory response indicating that the solution worked. As described herein, one or more of the tuples in the vector database may further be updated, redefined, etc. based on the user's interaction with the system (e.g., whether the user was satisfied with the solution presented or not).

FIG. 9 schematically illustrates a flow chart 900 for initially establishing a vector database and further training the vector database after establishment. At an operation 902, experts (e.g. HCP's) manually create initial tuples that each include embedding vectors and related solutions as described herein. The vector-database may then be populated with these expert curated tuples (e.g., the expert curated problem descriptions and related solutions). Thus, an expert database may be used as an initial starting point. For example, predefined gain correction settings may be used as or as a part of such an expert database. Such an expert database may include specific gain corrections for certain situations that may be entered by a user or identified by experts. For example, the situations may be defined by hierarchical inputs from a user or expert, where each gain correction setting is associated with a combination of inputs from the user or expert according to the hierarchical input. For example, a first input of the hierarchy may be related to a general sound category (e.g., loudness, speech, user's own voice, music, noise) that the user is experiencing. Upon inputting the first input, a second input may be relate to more details based on the first input. For example, if a sound category of "speech" is selected as the first input, the second input choices for a sound type may be for example, moderate speech in quiet, moderate male speech in quiet, moderate female speech in quiet, distant speech, or reverberant speech. A third input may further be presented to a user based on a combination of the first and second inputs. For example, if the first input sound category of "speech" is selected and the second input sound type of "moderate speech in quiet" is selected, the system may prompt the user or expert for a third input relating to the specific issue faced by the user, including options such as overall too loud, overall too soft, too bright/shrill, too dull, hollow and tinny, hollow and boomy, echo/reverberation, unintelligible, "s" sounds inaudible, or too much lisping. Each combination of the hierarchical inputs by a user or expert (e.g., the three inputs in the present example) may be associated with a predefined gain correction.

The different predefined gain corrections may therefore be used along with the inputs to define initial tuples that each include embedding vectors that therefore may be used as described herein. For example, with the three inputs and associated predefined gain corrections described above, the three inputs may be used as a natural language input and input into a fitting GPT to determine embeddings based on the natural language input (e.g., the combination of the three inputs). Such embeddings may then be stored as a tuple with the predefined gain correction in a vector database as described herein, and therefore may serve as an initial database on which to train the system to use new natural language inputs from a user to determine new gain corrections (or other setting changes) as described herein. For example, the three input selections described above of (i) sound category: speech; (ii) sound type: moderate speech in quiet; and (iii) issue: overall too loud may be used as a natural language input for a particular predefined gain correction. In this way, a vector database may be prepopulated with tuples and the inputs, their associated predefined setting level changes, and/or the tuples themselves may be used to train any aspect of a fitting GPT as described herein (e.g., an LLM conversational agent, text encoder, embedding decoder, etc.).

In various embodiments, an expert created embedding vector/related solution tuple or data pair may include an issue (e.g., speech not clear, background noise too loud, too tinny, too dull, too sharp) represented as an embedding vector with one or more dimensions as described herein, and that embedding vector may be associated with a solution that includes multiple different predefined adjustments to a hearing device or hearing system. For example, a given solution may include a predefined adjustment for several different characteristics, aspects, filters, etc. of a hearing device or system. For example, each embedding vector representative of an issue in an expert defined embedding vector/related solution tuple or data pair may be associated with multiple different predefined adjustments to characteristics, aspects, filters, etc. of a hearing device or system (e.g., solution may be associated with multiple predefined factors for adjustment such as bass level, mid level, treble level, volume level, noise reduction/filtering level, speech focus level, dynamic level, etc.). As such, for a given solution, multiple characteristics, aspects, filters, etc. of a hearing device or system may be adjusted and/or recommended to a user, and each expert defined solution may have associated predefined adjustment levels (or no adjustment level) for each of those characteristics, aspects, filters, etc. of a hearing device or system.

At an operation 904, manual adjustments to various components of a hearing system may be tracked and recorded to update or add new tuples to a problem/solution database. That is, any time a user makes an adjustment to a component of a hearing system, the hearing system may track these settings changes along with measured metrics, and the system may create new tuples (e.g., using the measured metrics such as noise measurements to create an embedding and the setting the user adjusted as the solution). At an operation 906, the system may further utilize follow-up answers from a user that are made in response to prompts from the system to update or add new tuples as described herein.

At an operation 908, confirmatory responses as described herein where a user may assent to a setting change being implemented may also be used to updated or add new tuples to a problem/solution database as described herein. At an operation 910, confirmatory responses that indicate a setting change worked to solve a user's issue may also be used to update or add new tuples. In other words, whenever a user assents to a change or confirms that a change worked, that information may be used to refine the stored tuples and/or an aspect of the fitting GPT described herein.

At an operation 912, new or updated tuples may be received at one or more devices of a hearing system via a network connection. As such, new or updated tuples (e.g., defined manually by experts, determined automatically by the systems of other end users, etc.) may be added to a user's system to enhance the system's functionality. At an operation 914, the system may further receive updates for its LLM conversation and/or text encoder to update the fitting GPT. In this way, the embeddings, machine learning models, algorithms, neural networks, etc. used to process natural language inputs/outputs, determine a fitting of an embedding vector to that of a tuple in a problem/solution database, etc. may also be updated (e.g., the weights of such models, algorithms, neural networks, may be updated over time). Such updating may occur via communication with one or more devices of the system over a network connection.

As such, the embodiments herein advantageously provide for systems and methods that allow an end user to address issues instantly and repetitively on their own without the need to set up appointment with an HCP. The solutions arrived at may also be better than those arrived at in HCP sessions, because the model can use additional metrics (noise floor estimation, signal-to-noise ratio, etc.) as information input to solve an issue in each situation, and the user can engage in an iterative process with the system in real time to continue looking for adjustments and solutions until a satisfactory one is reached. Such systems and methods may also advantageously help users who inherently are unlikely to go to HCP follow-up sessions after getting a new hearing device.

Such advantages provide for better clinical outcomes, as users will be able to achieve improved audiological performance, comfort, and/or sound quality. The systems and methods herein are also configured for continuous improvement and learning, so that the systems and methods improve over time as users utilize the various embodiments described herein, further improving outcomes for users. In other words, the systems, models, and machine learning algorithms used to implement the embodiments herein may be improved by collecting feedback (e.g., ratings, acknowledgments) from users for applied configurations and configuration changes, which can be used as labels for learning (e.g., knowledge about true improvements); a bad rating or a user's veto could also indicate uncertainty of the steering unit and a need for gathering more representative data for the given situation.

The embodiments herein also advantageously may learn users' preferences (e.g., a system trained on one user's habits, needs, and preferences may evolve to function differently than another user's system). Each user's system may therefore have unique data. That unique data may be abstracted and used for user groups profiles, such that recommendations and/or predictions to users based on their own and/or other users' feedback may also be generated (e.g., users of a similar age, condition, etc. may get similar recommendations). Data about particular environmental scenarios or particular geographic locations may further be derived from user behavior and metrics gathered by the system, so that similar settings may be implemented for users that are in the same place or in a similar scenario/environment.

Advantageously, the safety of the system may also be enhanced by having human control entities at several levels (e.g., user themselves, experts like HCP, manufacturer, regulatory body) to acknowledge decisions by the system to ensure compliance with medical regulations (e.g., medical safety, application/network security) and/or performance as intended, i.e., according to requirements/specification (machine learning algorithm safety as well as machine learning algorithm security: increase users' safety/security and hearing devices' quality, eventual verification—according to users' requirements—to make up for limited product verification of machine learning algorithm systems and anticipate unexpected situations as quasi verification of the "black box" in the field through experts instances). Verification of the systems herein may also reduce inherent limitations of the machine learning algorithms of missing determinism and transparency (e.g., what has been learnt exactly) and its predictions implying uncertainty.

Various components of the systems described herein may further be used, for example, as an artificial intelligence (AI)-based hearing intention translator and/or self-adjustment advisor. For example, components of the fitting GPT 402 such as the LLM conversational agent 404 of FIG. 4 may be used as an AI-based hearing intention translator and/or self-adjustment advisor. As described herein, hearing devices allow many possibilities to individualize their fitting. Such customization may be done by a user with their hearing device or a related user device (e.g., on a situational basis with the hearing aid buttons or a self-adjustment application on a smart device), or with help of a health care provider (HCP). However, an end-user may not know about all the possible self-adjustments he/she can make, and an end user may not know the consequences that a particular setting or change to a setting may have. An HCP may also not be aware about all the possibilities for adjustment and/or the consequences and limitations of all fitting individualization options for a given hearing device and associated fitting software. In addition, even if an HCP is aware of most or all of the possible settings adjustments, it may be difficult to translate what an end-user complains about or would desire, to appropriately adapt the hearing device fitting. End-users may also struggle to identify possible self-adjustments to the situational fittings which might provide a benefit in a particular situation. All this may lead to situations where hearing devices perform below an optimal, individualized fitting for particular listening situations and for particular users.

As such, the various embodiments described herein further advantageously provide for systems, apparatuses, methods, and computer-readable media for translating an end-user's verbal comments, speech, natural language inputs, etc. about his/her needs and situational listening intention (e.g., what the end user would like to accomplish in a given situation). Such embodiments may utilize a chat bot or artificial intelligence unit trained to translate typical end-user's comments, speech, natural language inputs, etc. to a technically understandable interpretation. Such interpretations could be provided to: (i) an HCP, who might receive the interpretation at an HCP computing device, upon which is also installed a software tool with which the HCP may implement adjustments to a fitting of a hearing device based on the translation; (ii) to an end-user via a display of a device of a hearing system (e.g., the user device 14 of FIGS. 1 and 2, the external device 80 of FIG. 2, etc.). For example, a chat bot or other AI-based hearing intention translator may operate on a smart device such as a tablet, smartwatch, mobile or smart phone, smart glasses, etc. As such, the user may use the chat bot or other AI-based hearing intention translator to interpret their comments about their hearing device, such as for purposes of (i) self-adjustment of a hearing device; (ii) to provide the interpretation to an HCP (or HCP computing device) for adjustment of the hearing device (or other device of a hearing system) by the HCP); or (iii) to provide the interpretation to a fitting GPT and/or vector database for automated adjustment of a hearing system or provision of a recommendation for adjusting a hearing system as described herein. In various embodiments, such a chat bot or AI-based hearing intention translator may be or may operate similar to the LLM conversational agent 404 of FIG. 4 as described herein. Such a chat bot or AI-based hearing intention translator may operate on a user device, on an HCP computing device, on a cloud computing device (e.g., the remote server 72 of FIG. 2), or any combination thereof.

As such, an end-user may get advice from a chat bot or AI-based hearing intention translator how to adapt the self-adjustment of his/her hearing device in a user's current situation based on the user's verbalized listening intention. As described herein, various components of a hearing system (e.g., the hearing device 12, the user device 14, the external device 80) may also measure certain metrics (e.g., current acoustical properties of an environment) or take note of current settings of a component of a hearing system, and take that information into account in translating the input from the user and/or in making a recommendation based on the input form the user. As such, a steering unit of a hearing device may also automatedly adjust the current actuators or classification depending on the extracted listening intention as described herein. The system may also inform an end-user about a potential malfunctioning of the device, if the algorithm/model/neural network links the stated problem to a failure of a physical component of the device (e.g., a polluted receiver, blocked microphone inlets, etc.). As such, the various embodiments described herein include, a translation tool that may be used to facilitate communication between either or both of a user and an HCP and a user and an automated hearing device adjustment system. Such a translator may further be used to translate between languages, so that an HCP may treat or work with a user to adjust a hearing device even if the HCP and the end user do not speak the same language. In other embodiments, the translation may be in the same language, but the system may merely translate inputs from an end user in that language into outputs of the same language that better articulate the user's problems/issues, requests, intentions, etc.

Described herein are therefore advantageous systems, apparatuses, methods, and computer-readable media for AI-based translation tools that identify an end-user's comments on his/her listening intentions and/or situational difficulties and translate/rephrase it in a way that an HCP can understand or for which the system may make a meaningful proposal for self-adjustment. This may provide for more effective self-adjustment of devices and/or more effective communication between end-users and HCPs, resulting in less time wasted on inappropriate fittings that may have been recommended or set due to miscommunication between users and HCPs, or due to poor HCP or end user training on the possibilities for adjustments of devices and when to use such settings. The various embodiments herein therefore provide for better first fits, less ineffective acclimatization periods, new possibilities in self-fitting, etc.

Figure 10:
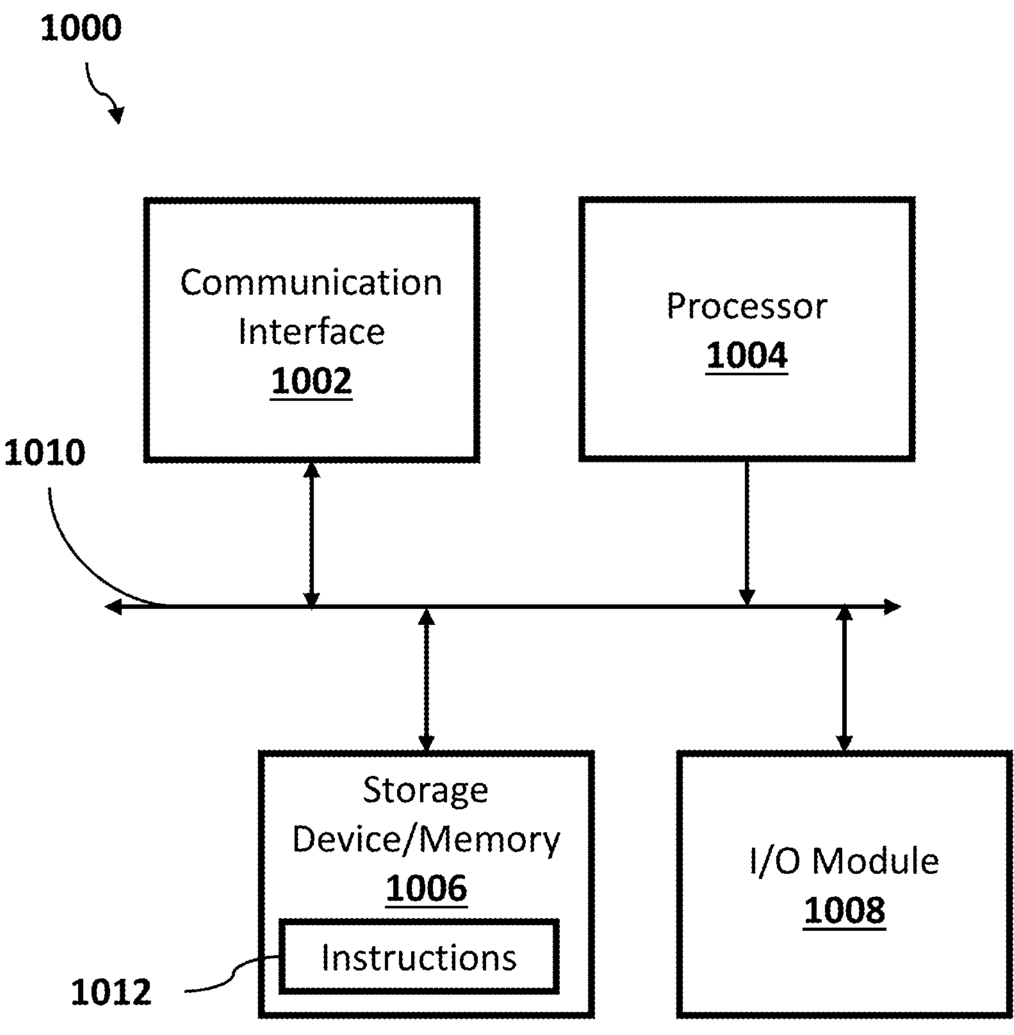
FIG. 10 schematically illustrates an exemplary computing device.

FIG. 10 illustrates an exemplary computing device 1000 that may be specifically configured to perform one or more of the processes described herein. Any of the systems and/or devices described herein may be implemented by computing device 1000.

As shown in FIG. 10, computing device 1000 may include a communication interface 1002, a processor 1004, a storage device 1006, and an input/output ("I/O") module 1008 communicatively connected one to another via a communication infrastructure 1010. While an exemplary computing device 1000 is shown in FIG. 10, the components illustrated in FIG. 10 are not intended to be limiting. Additional or alternative components may be used in other embodiments. Components of computing device 1000 shown in FIG. 10 will now be described in additional detail.

Communication interface 1002 may be configured to communicate with one or more computing devices. Examples of communication interface 1002 include, without limitation, a wired network interface (such as a network interface card), a wireless network interface (such as a wireless network interface card), a modem, an audio/video connection, and any other suitable interface.

Processor 1004 generally represents any type or form of processing unit capable of processing data and/or interpreting, executing, and/or directing execution of one or more of the instructions, processes, and/or operations described herein. Processor 1004 may perform operations by executing computer-executable instructions 1012 (e.g., an application, software, code, and/or other executable data instance) stored in storage device 1006.

Storage device 1006 may also be referred to as memory, and may include one or more data storage media, devices, or configurations and may employ any type, form, and combination of data storage media and/or device. For example, storage device 1006 may include, but is not limited to, any combination of the non-volatile media and/or volatile media described herein. Electronic data, including data described herein, may be temporarily and/or permanently stored in storage device 1006. For example, data representative of computer-executable instructions 1012 configured to direct processor 1004 to perform any of the operations described herein may be stored within storage device 1006. In some examples, data may be arranged in one or more databases residing within storage device 1006.

I/O module 1008 may include one or more I/O modules configured to receive user input and provide user output. I/O module 1008 may include any hardware, firmware, software, or combination thereof supportive of input and output capabilities. For example, I/O module 1008 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1008 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1008 is configured to provide graphical data to a display for presentation to a user. The graphical data may be representative of one or more graphical user interfaces and/or any other graphical content as may serve a particular implementation.

While the principles of the disclosure have been described above in connection with specific devices and methods, it is to be clearly understood that this description is made only by way of example and not as limitation on the scope of the invention. The above described preferred embodiments are intended to illustrate the principles of the invention, but not to limit the scope of the invention. Various other embodiments and modifications to those preferred embodiments may be made by those skilled in the art without departing from the scope of the present invention that is solely defined by the claims. In the claims, the word "comprising" does not exclude other elements or steps, and the indefinite article "a" or "an" does not exclude a plurality. A single processor or controller or other unit may fulfil the functions of several items recited in the claims. The mere fact that certain measures are recited in mutually different dependent claims does not indicate that a combination of these measures cannot be used to advantage. Any reference signs in the claims should not be construed as limiting the scope.

What is claimed is:

1. A fitting apparatus for a hearing device comprising:
a processor; and
a memory having stored thereon:
non-transitory computer readable instructions executable by the processor, and
a plurality of embedding vectors and related solutions for possible hearing issues with the hearing device or a computing device,
and further wherein, upon execution of the instructions, the fitting apparatus is configured to:
receive, via a user interface of the hearing device or the computing device, a first signal indicative of a natural language input, wherein the natural language input is indicative of an issue experienced by a user with the hearing device or the computing device;
determine an embedding based on the natural language input, wherein the embedding comprises embeddings related to multiple dimensions;
generate, based on the embedding, a first embedding vector, wherein the first embedding vector is indicative of values associated with each of the embeddings related to multiple dimensions;
determine a closest match between the first embedding vector and an embedding vector of the plurality of embedding vectors; and
send, to the user interface of the hearing device or the computing device, a second signal indicative of a reply output, the reply output comprising information related to a solution of the related solutions for the issue experienced by the user.

2. The fitting apparatus for the hearing device of claim 1, wherein the embedding is a first embedding, and wherein the fitting apparatus is further configured to, upon execution of the instructions:
receive a third signal indicative of a setting of the hearing device or the computing device; and
determine a second embedding based on the setting, wherein the first embedding vector is generated based on both the first embedding and the second embedding.

3. The fitting apparatus for the hearing device of claim 2, wherein the setting of the hearing device or the computing device comprises at least one of:
a fitting parameter set of a hearing device;
a type of the hearing device;
a coupling setting or type of the hearing device;
a feedback threshold of the hearing device;
a real ear transfer function setting of the hearing device;
a target gain of the hearing device;
actual gain of the hearing device;
an actuator setting of the hearing device;
actual feedback stability of the hearing device; or
a hardware test parameter of the hearing device.

4. The fitting apparatus for the hearing device of claim 2, wherein the fitting apparatus is further configured to, upon execution of the instructions:
receive a fourth signal indicative of a metric measured by the hearing device or the computing device; and
determine a third embedding based on the setting, wherein the first embedding vector is generated based on both the first embedding, the second embedding, and the third embedding.

5. The fitting apparatus for the hearing device of claim 4, wherein the metric comprises at least one of:

a signal level;

a noise floor estimation;

a signal-to-noise ratio;

a classification of a sound source; or an estimated listening intention.

6. The fitting apparatus for the hearing device of claim 1, wherein the computing device comprises at least one of a user device or an external device.

7. The fitting apparatus for the hearing device of claim 1, wherein the natural language input further comprises temporal information related to the issue experienced by the user, the temporal information indicative of whether the issue is being currently experienced or was previously experienced by the user.

8. The fitting apparatus for the hearing device of claim 1, wherein the fitting apparatus is further configured to, upon execution of the instructions:

receive, via the user interface of the hearing device or the computing device, a third signal indicative of a confirmatory response to the reply output, the confirmatory response indicative of a user assent to implementing the solution; and implement the solution in the hearing device or the computing device, or send an instruction to implement the solution to the hearing device or the computing device.

9. The fitting apparatus for the hearing device of claim 1, wherein the fitting apparatus is further configured to, upon execution of the instructions:

send, to the user interface of the hearing device or the computing device, a third signal indicative of a request to confirm an efficacy of the solution for the issue; and receive, via the user interface of the hearing device or the computing device, a fourth signal indicative of a confirmatory response to the request.

10. The fitting apparatus for the hearing device of claim 9, wherein the fitting apparatus is further configured to, upon execution of the instructions, update the plurality of embedding vectors and/or the related solutions based on the confirmatory response to the request.

11. The fitting apparatus for the hearing device of claim 1, wherein the fitting apparatus is further configured to, upon execution of the instructions:

send, prior to sending the second signal indicative of the reply output, a third signal indicative of a follow-up request to the user interface of the hearing device or the computing device, wherein the follow-up request requests more information related to the issue experienced by the user; and receive, via the user interface of the hearing device or the computing device, a fourth signal indicative of a follow-up answer to the follow-up request, wherein the first embedding vector is further determined at least in part based on the follow-up request.

12. The fitting apparatus for the hearing device of claim 1, wherein the natural language input comprises at least one of:

text entered by the user through a keyboard of the user interface of the hearing device or the computing device; or speech spoken by the user and sensed by a sound detector of the hearing device or the computing device.

13. The fitting apparatus for the hearing device of claim 1, wherein each of the plurality of embedding vectors and the related solutions are manually defined based on previously identified problems with hearing devices and the previously identified problems' respective solutions.

14. The fitting apparatus for the hearing device of claim 1, wherein the fitting apparatus is further configured to, upon execution of the instructions:

determine, based on first signal indicative of the natural language input, a translation of the natural language input; and send, to a computing device associated with a health care provider, a third signal indicative of the translation.

15. A method for fitting a hearing device comprising:

receiving, by a processor via a user interface of the hearing device or a computing device, a first signal indicative of a natural language input, wherein the natural language input is indicative of an issue experienced by a user with the hearing device or the computing device;

determining, by the processor, a first embedding based on the natural language input, wherein the first embedding is related to a first dimension of multiple dimensions;

receiving, by the processor, a second signal indicative of:

a setting of the hearing device or the computing device, or a metric measured by the hearing device or the computing device;

determining, by the processor, a second embedding based on the setting or the metric, wherein the second embedding is related to a second dimension of multiple dimensions;

generating, by the processor based on the first embedding and the second embedding, a first embedding vector, wherein the first embedding vector is indicative of values associated with each of the first embedding related to the first dimension and the second embedding related to the second dimension;

determining, by the processor, a closest match between the first embedding vector and an embedding vector of an embedding vector of a plurality of embedding vectors, wherein each of the plurality of embedding vectors is associated with one of a plurality of related solutions for possible hearing issues with the hearing device or the computing device; and sending, by the processor to the user interface of the hearing device or the computing device, a third signal indicative of a reply output, the reply output comprising information related to a solution of the related solutions for the issue experienced by the user.

16. A fitting apparatus for a hearing device comprising:

a processor; and a memory having stored thereon:

non-transitory computer readable instructions executable by the processor, and a plurality of embedding vectors and related solutions for possible hearing issues with the hearing device or a computing device, and further wherein, upon execution of the instructions, the fitting apparatus is configured to:

receive, via a user interface of the hearing device or the computing device, a first signal indicative of a natural language input, wherein the natural language input is indicative of an issue experienced by a user with the hearing device or the computing device;

determine an embedding based on the natural language input;

send, after receiving the first signal indicative of the natural language input, a second signal indicative of a follow-up request to the user interface of the hearing device or the computing device, wherein the follow-up request requests more information related to the issue experienced by the user; and receive, via the user interface of the hearing device or the computing device, a third signal indicative of a follow-up answer to the follow-up request, generate, based on the embedding and at least in part based on the follow-up request or the follow-up answer, a first embedding vector;

determine a closest match between the first embedding vector and an embedding vector of the plurality of embedding vectors; and send, to the user interface of the hearing device or the computing device, a fourth signal indicative of a reply output, the reply output comprising information related to a solution of the related solutions for the issue experienced by the user.

17. The fitting apparatus for the hearing device of claim 16, wherein the setting of the hearing device or the computing device comprises at least one of:

a fitting parameter set of a hearing device;

a type of the hearing device;

a coupling setting or type of the hearing device;

a feedback threshold of the hearing device;

a real ear transfer function setting of the hearing device;

a target gain of the hearing device;

actual gain of the hearing device;

an actuator setting of the hearing device;

actual feedback stability of the hearing device; or a hardware test parameter of the hearing device.

18. The fitting apparatus for the hearing device of claim 16, wherein the embedding based on the natural language input comprises embeddings related to multiple dimensions, wherein the first embedding vector is indicative of values associated with each of the embeddings related to multiple dimensions.

19. The fitting apparatus for the hearing device of claim 16, wherein the natural language input further comprises temporal information related to the issue experienced by the user, the temporal information indicative of whether the issue is being currently experienced or was previously experienced by the user.

20. The fitting apparatus for the hearing device of claim 16, wherein the fitting apparatus is further configured to, upon execution of the instructions:

receive, via the user interface of the hearing device or the computing device, a fifth signal indicative of a confirmatory response to the reply output, the confirmatory response indicative of a user assent to implementing the solution; and implement the solution in the hearing device or the computing device, or send an instruction to implement the solution to the hearing device or the computing device.

* * * * *